(12) United States Patent
Ziemer et al.

(10) Patent No.: US 7,135,434 B2
(45) Date of Patent: Nov. 14, 2006

(54) COMBINATIONS OF HERBICIDES AND SAFENERS

(75) Inventors: Frank Ziemer, Kriftel (DE); Lothar Willms, Hofheim (DE); Hermann Bieringer, Eppstein (DE); Erwin Hacker, Hochheim (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 268 days.

(21) Appl. No.: 10/265,925

(22) Filed: Oct. 7, 2002

(65) Prior Publication Data

US 2003/0171220 A1  Sep. 11, 2003

Related U.S. Application Data

(62) Division of application No. 09/337,135, filed on Jun. 21, 1999, now Pat. No. 6,511,940.

(30) Foreign Application Priority Data

Jun. 23, 1998  (DE) ................................ 198 27 855

(51) Int. Cl.
*A01N 25/32* (2006.01)
*A01N 43/50* (2006.01)
*A01P 13/00* (2006.01)

(52) U.S. Cl. ...................... 504/130; 504/139; 504/140; 504/282

(58) Field of Classification Search ................ 504/106, 504/129, 134, 130, 139, 140, 282
See application file for complete search history.

(56) References Cited

U.S. PATENT DOCUMENTS

| | | | |
|---|---|---|---|
| 4,938,796 A | 7/1990 | Buren et al. | |
| 5,441,922 A | 8/1995 | Ort et al. | |
| 5,516,750 A | 5/1996 | Willms et al. | 504/116 |
| 5,627,131 A | 5/1997 | Shribbs et al. | 548/248 |
| 5,846,907 A * | 12/1998 | von Deyn et al. | 504/221 |
| 5,849,928 A | 12/1998 | Hawkins | 504/105 |
| 6,140,271 A * | 10/2000 | Turner et al. | 504/282 |

FOREIGN PATENT DOCUMENTS

| | | |
|---|---|---|
| EP | 0298680 | 1/1989 |
| EP | 496631 | 7/1992 |
| EP | 0551650 | 7/1993 |
| JP | 55157504 | 12/1980 |
| WO | WO 96/21357 | 7/1996 |
| WO | WO 97/01550 | 1/1997 |

OTHER PUBLICATIONS

Prisbylla et al., "The Novel Mechanism of Action of the Herbicidal Triketones", Brighton Crop Protection Conference—Weeds, 1993, pp. 731-738.

* cited by examiner

*Primary Examiner*—S. Mark Clardy
(74) *Attorney, Agent, or Firm*—Frommer Lawrence & Haug LLP

(57) ABSTRACT

This invention provides for, inter alia, a herbicidal composition comprising a mixture of: A. a herbicidally effective amount of at least one compound of the formula

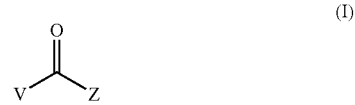

(I)

where V and Z are defined in the specification; and B. an antidote.

4 Claims, No Drawings

COMBINATIONS OF HERBICIDES AND SAFENERS

RELATED APPLICATIONS

This application is a divisional of application U.S. Ser. No. 09/337,135 filed Jun. 21, 1999, now U.S. Pat. No. 6,511,940 which in turn claims priority under 35 USC § 119 to German application Serial No. 198 27 855.1, filed Jun. 23, 1998.

DESCRIPTION

The invention relates to the technical field of the crop protection products, in particular herbicide/antidote combinations (active substance/safener combinations) which are outstandingly suitable for the use against competing harmful plants in crops of useful plants.

Some of the more recent herbicidal active substances which inhibit p-hydroxyphenylpyruvate dioxygenase (HPPDO) have very good use characteristics and can be employed at very low application rates against a broad spectrum of grass weeds and broad-leaved weeds (see, for example, M. P. Prisbylla et al., Brighton Crop Protection Conference—Weeds (1993), 731–738).

However, many of these highly efficient active substances are not fully compatible with (i.e. not sufficiently selective in) some important crop plants such as maize, rice or cereals, so that their use is strictly limited. In certain crops, they can therefore not be employed, or at such low application rates that the desired broad herbicidal efficacy towards harmful plants is not guaranteed. Specifically, many of the above-mentioned herbicides cannot be employed fully selectively against harmful plants in maize, rice, cereals or some other crops.

To overcome these disadvantages, it is known to employ herbicidal active substances in combination with a so-called safener or antidote. A safener for the purpose of the invention is a compound or a mixture of compounds which compensates for, or reduces, the phytotoxic properties of a herbicide towards useful plants without substantially reducing the herbicidal action against harmful plants.

The identification of a safener for a particular class of herbicides remains a difficult task since the exact mechanisms by which a safener reduces the harmful effect of herbicides are unknown. The fact that a compound in combination with a particular herbicide acts as a safener allows no conclusions as to whether such a compound also acts as a safener with other classes of herbicide. Thus, it has emerged that, when using safeners for protecting the useful plants from herbicide damage, the safeners may still have a number of disadvantages in many cases. These are:
- the safener reduces the action of the herbicides against the harmful plants,
- the useful-plant-protecting properties are insufficient,
- in combination with a given herbicide, the spectrum of the useful plants in which the safener/herbicide is to be used is insufficiently wide,
- a given safener may not be combined with a sufficiently large number of herbicides.

It was an object of the present invention to identify compounds which, in combination with the abovementioned herbicides are suitable for increasing the selectivity of these herbicides towards important crop plants.

Surprisingly, a group of compounds has now been found which, together with specific herbicides which act as HPPDO inhibitors, increase the selectivity of these herbicides towards important crop plants.

The invention therefore relates to a herbicidally active composition comprising a mixture of
A. a herbicidally active amount of one or more compounds of the formula (I)

(I)

in which
V is a radical selected from the group consisting of (V1) to (V4),

(V1)

(V2)

(V3)

(V4)

where the symbols and indices have the following meanings:

R is hydrogen, $(C_1-C_4)$alkoxycarbonyl, $(C_1-C_4)$haloalkoxycarbonyl, COOH, cyano, preferably hydrogen, $(C_1-C_4)$alkoxycarbonyl;

$R^1$ is hydrogen or a $(C_1-C_7)$carbon-containing radical such as $(C_1-C_4)$alkyl, $(C_2-C_4)$alkenyl, $(C_2-C_4)$alkynyl, $(C_3-C_7)$cycloalkyl, $(C_3-C_7)$cycloalkenyl, $(C_1-C_4)$alkyl-$(C_3-C_7)$cycloalkyl, $(C_3-C_7)$halocycloalkyl, $(C_1-C_4)$alkylthiocycloalkyl, $(C_1-C_4)$haloalkyl, $(C_2-C_4)$haloalkenyl, preferably $(C_3-C_7)$cycloalkyl, $(C_1-C_4)$alkyl-$(C_3-C_7)$cycloalkyl;

$R^2$ is hydrogen, $(C_1-C_4)$alkyl, $(C_1-C_4)$alkoxy, $(C_1-C_4)$haloalkyl, halogen, $(C_1-C_4)$haloalkoxy, cyano, nitro, preferably hydrogen;

$R^3$ is hydrogen or a $(C_1-C_4)$carbon-containing radical such as $(C_1-C_4)$alkyl, $(C_2-C_4)$alkenyl, $(C_2-C_4)$alkynyl, $(C_1-C_4)$haloalkyl, $(C_1-C_4)$alkoxy-$(C_1-C_4)$alkyl, $(C_1-C_4)$alkylcarbonyl, $(C_1-C_4)$alkylsulfonyl, $(C_1-C_4)$halo-alkylsulfonyl, arylsulfonyl, arylcarbonyl-$(C_1-C_4)$alkyl, aryl-$(C_1-C_4)$alkyl, preferably hydrogen, $(C_1-C_4)$alkyl, arylsulfonyl, benzyl;

R⁴ is hydrogen or a $(C_1-C_7)$carbon-containing radical such as $(C_1-C_4)$alkyl, $(C_2-C_4)$alkenyl, $(C_2-C_4)$alkynyl, $(C_1-C_4)$haloalkyl, phenyl, benzyl, preferably $(C_1-C_4)$alkyl;

R⁵ is a $(C_1-C_{12})$carbon-containing radical such as $(C_1-C_4)$alkyl, $(C_1-C_4)$alkoxy, $(C_1-C_4)$alkoxy-$(C_1-C_4)$alkyl, $(C_1-C_4)$dialkoxy-$(C_1-C_4)$alkyl, $(C_1-C_4)$alkylthio, halogen, substituted or unsubstituted aryl, tetrahydropyran-4-yl, tetrahydropyran-3-yl, tetrahydrothiopyran-3-yl, 1-methylthio-cyclopropyl, 2-ethylthiopropyl, preferably $(C_1-C_4)$alkyl, $(C_1-C_4)$alkoxy;

R⁶ is hydroxyl or a $(C_1-C_4)$carbon-containing radical such as $(C_1-C_4)$alkoxy, $(C_1-C_4)$haloalkoxy, formyloxy, $(C_1-C_4)$alkylcarbonyloxy, $(C_1-C_4)$alkylsulfonyloxy, $(C_1-C_4)$alkylthio, $(C_1-C_4)$haloalkylthio, $(C_1-C_4)$alkylsulfinyl, $(C_1-C_4)$alkylsulfonyl, preferably hydroxyl, $(C_1-C_4)$alkoxy;

R⁷ is a $(C_1-C_7)$carbon-containing radical such as $(C_1-C_4)$alkyl, $(C_1-C_4)$haloalkyl, $(C_3-C_7)$cycloalkyl, $(C_1-C_4)$alkyl-$(C_3-C_7)$cycloalkyl, $(C_3-C_7)$halocycloalkyl, preferably $(C_3-C_7)$cycloalkyl;

R⁸ is cyano or a $(C_1-C_4)$carbon-containing radical such as $(C_1-C_4)$alkoxycarbonyl, $(C_1-C_4)$alkylcarbonyl, $(C_1-C_4)$alkylsulfonyl, $(C_1-C_4)$alkylsulfinyl, $(C_1-C_4)$alkylthio, $(C_1-C_4)$alkylaminocarbonyl, $(C_1-C_4)$dialkylaminocarbonyl, preferably cyano;

m is an integer from 0 to 6, preferably 0 to 3, and Z is a radical selected from the group consisting of (Z1) to (Z4),

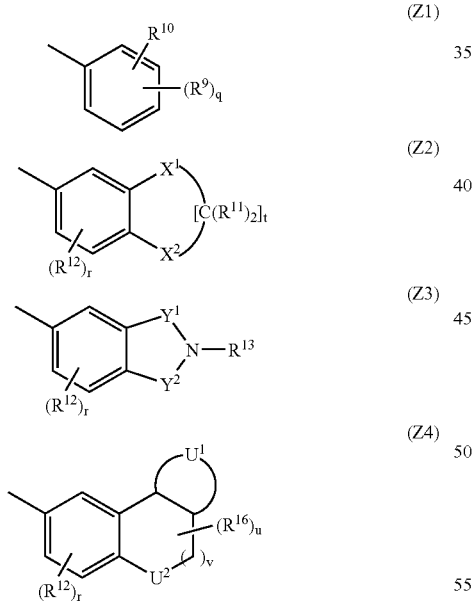

where the symbols and indices have the following meanings:

R⁹ is nitro, amino, halogen or a $(C_1-C_8)$carbon-containing radical such as $(C_1-C_4)$alkyl, $(C_2-C_4)$alkenyl, $(C_2-C_4)$alkynyl, $(C_1-C_4)$haloalkyl, $(C_2-C_4)$haloalkenyl, $(C_2-C_4)$haloalkynyl, $(C_1-C_4)$haloalkoxy, $(C_1-C_4)$haloalkylthio, $(C_1-C_4)$alkoxycarbonyl, $(C_1-C_4)$alkylsulfonyl, $(C_1-C_4)$alkylsulfinyl, $(C_1-C_4)$alkylthio, arylthio, arylsulfonyl, arylsulfinyl, arylthio, $(C_1-C_4)$alkoxy, $(C_1-C_4)$alkoxy-$(C_1-C_4)$alkoxy, $(C_1-C_4)$alkylcarbonyl, $(C_1-C_4)$alkylaminosulfonyl, $(C_1-C_4)$dialkylaminosulfonyl, $(C_1-C_4)$alkylcarbamoyl, $(C_1-C_4)$dialkylcarbamoyl, $(C_1-C_4)$alkoxy-$(C_1-C_4)$alkyl, phenoxy, cyano, aryl, alkylamino, dialkylamino, preferably $(C_1-C_4)$alkyl, $(C_1-C_4)$haloalkyl, $(C_1-C_4)$haloalkoxy, $(C_1-C_4)$alkylsulfonyl, $(C_1-C_4)$alkylsulfonyloxy, $(C_1-C_4)$alkylsulfonylamino, $(C_1-C_4)$alkoxycarbonyl;

R¹⁰ is substituted or unsubstituted benzyl, substituted or unsubstituted heteroaryl, heterocyclyl, preferably furanyl, thiazolyl, triazolyl, pyrazolyl, oxazolyl, isoxazolyl, isoxazolinyl, morpholino, and imidazolyl; heteroaryl-$(C_1-C_4)$alkyl, preferably triazolylmethyl, pyrazolylmethyl, thiazolylmethyl, di-$(C_1-C_4)$alkylphosphono-$(C_1-C_4)$alkyl, preferably diethylphosphonomethyl, dimethylphosphonomethyl or $SF_5$;

R¹¹ is identical or different hydrogen, $(C_1-C_4)$alkyl, halogen, preferably $(C_1-C_4)$alkyl;

R¹² is identical or different $(C_1-C_4)$alkyl, $(C_2-C_4)$alkenyl, $(C_2-C_4)$alkynyl, halogen, $(C_1-C_4)$haloalkyl, $(C_2-C_4)$haloalkenyl, $(C_2-C_4)$haloalkynyl, $(C_1-C_4)$haloalkoxy, $(C_1-C_4)$haloalkylthio, $(C_1-C_4)$alkoxycarbonyl, $(C_1-C_4)$alkylsulfonyl, $(C_1-C_4)$haloalkylsulfonyl, $(C_1-C_4)$alkylsulfinyl, $(C_1-C_4)$haloalkylsulfinyl, $(C_1-C_4)$alkylthio, $(C_1-C_4)$alkoxy, $(C_1-C_4)$alkylcarbonyl, $(C_1-C_4)$alkylaminosulfonyl, $(C_1-C_4)$dialkylaminosulfonyl, $(C_1-C_4)$alkylcarbamoyl, $(C_1-C_4)$dialkylcarbamoyl, $(C_1-C_4)$alkoxyalkyl, phenoxy, nitro, cyano, aryl, di-$(C_1-C_4)$alkylphosphono-$(C_1-C_4)$alkyl, preferably $(C_1-C_4)$alkyl, halogen, $(C_1-C_4)$haloalkyl, $(C_1-C_4)$alkylsulfonyl, $(C_1-C_4)$alkoxycarbonyl;

q is 0, 1, 2, 3 or 4;

r is 0, 1, 2 or 3;

t is 1 or 2;

u is 0, 1 or 2;

v is 1 or 2;

$X^1$ is O, $CR^{14}R^{15}$, CHOH, C=O, C=NO$(C_1-C_4)$alkyl;

$X^2$ is O, S, SO, $SO_2$, $CH_2$, NH, N$(C_1-C_4)$alkyl, $NSO_2$ $(C_1-C_4)$alkyl, preferably $SO_2$;

U¹ together with the linked carbon atoms forms a carbocyclic or heterocyclic ring which can be aromatic or fully or partially saturated, preferably a pyrazole, imidazole, pyrrole, pyridine, pyrimidine, thiazole, thienyl, oxazole or furan ring;

$U^2$ is O, S, SO, $SO_2$, $CH_2$, NH, N$(C_1-C_4)$alkyl, $NSO_2$ $(C_1-C_4)$alkyl, preferably $SO_2$;

R¹³ is hydrogen, $(C_1-C_4)$alkyl, $(C_3-C_7)$cycloalkyl, $(C_2-C_4)$alkenyl, $(C_2-C_4)$alkynyl, optionally substituted phenyl, optionally substituted benzyl, $(C_1-C_4)$acyl;

$R^{14}$, $R^{15}$ is identical or different hydrogen, $(C_1-C_4)$alkyl, $(C_1-C_4)$alkoxy, $(C_1-C_4)$haloalkoxy, $(C_1-C_4)$alkylthio, $(C_1-C_4)$haloalkylthio or $R^{14}$ and $R^{15}$ together form one of the groups —O—$(CH_2)_2$—O—, —O—$(CH_2)_3$—O—, S—$(CH_2)_2$—S—, —S—$(CH_2)_3$—S—, —$(CH_2)_4$—, —$(CH_2)_5$—;

R¹⁶ is $(C_1-C_2)$alkyl;

$Y^1$, $Y^2$ are $SO_2$ or CO, with the proviso that $Y^1 \neq Y^2$, and

B. an antidote-effective amount of one or more compounds selected from the groups consisting of a) to e):

a) compounds of the formulae (II) to (IV),

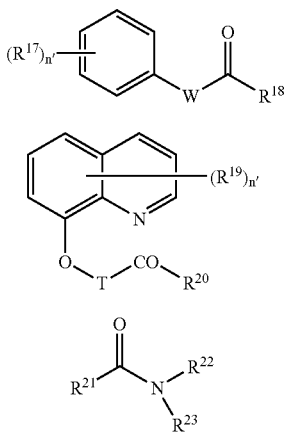

where the symbols and indices having the following meanings:
n' is a natural number from 1 to 5, preferably 1 to 3;
T is a ($C_1$ or $C_2$)-alkanediyl chain which is unsubstituted or substituted by one or two ($C_1$–$C_4$)alkyl radicals or by [($C_1$–$C_3$)-alkoxy]carbonyl;
W is an unsubstituted or substituted divalent heterocyclic radical selected from the group consisting of the partially unsaturated or aromatic five-ringed heterocycles having 1 to 3 hetero ring atoms of the type N or O, the ring containing at least one nitrogen atom and not more than one oxygen atom, preferably a radical selected from the group consisting of (W1) to (W4),

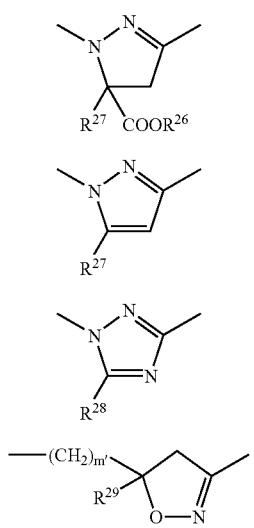

m' is 0 or 1;
$R^{17}$, $R^{19}$ are identical or different hydrogen, halogen, ($C_1$–$C_4$)alkyl, ($C_1$–$C_4$)alkoxy, nitro or ($C_1$–$C_4$)haloalkyl;
$R^{18}$, $R^{20}$ are identical or different $OR^{24}$, $SR^{24}$ or $NR^{24}R^{25}$ or a saturated or unsaturated 3- to 7-membered heterocycle having at least one nitrogen atom and up to 3 hetero atoms which is linked to the carbonyl group in (II) or (III) via the nitrogen atom and which is unsubstituted or substituted by radicals selected from the group consisting of ($C_1$–$C_4$)alkyl, ($C_1$–$C_4$)alkoxy or optionally substituted phenyl, preferably a radical of the formula $OR^{24}$, $NHR^{25}$ or $N(CH_3)_2$, in particular of the formula $OR^{24}$;
$R^{24}$ is hydrogen or an unsubstituted or substituted aliphatic hydrocarbon radical, preferably having in total 1 to 18 carbon atoms;
$R^{25}$ is hydrogen, ($C_1$–$C_6$)alkyl, ($C_1$–$C_6$)alkoxy or substituted or unsubstituted phenyl;
$R^{26}$ is hydrogen, ($C_1$–$C_8$)alkyl, ($C_1$–$C_8$)haloalkyl, ($C_1$–$C_4$)alkoxy-($C_1$–$C_4$)alkyl, ($C_1$–$C_6$)hydroxyalkyl, ($C_3$–$C_{12}$)cycloalkyl or tri-($C_1$–$C_4$)-alkylsilyl;
$R^{27}$, $R^{28}$, $R^{29}$ are identical or different hydrogen, ($C_1$–$C_8$) alkyl, ($C_1$–$C_8$)haloalkyl, ($C_3$–$C_{12}$)cycloalkyl or substituted or unsubstituted phenyl;
$R^{21}$ is ($C_1$–$C_4$)alkyl, ($C_1$–$C_4$)haloalkyl, ($C_2$–$C_4$)alkenyl, ($C_2$–$C_4$)haloalkenyl, ($C_3$–$C_7$)cycloalkyl, preferably dichloromethyl;
$R^{22}$, $R^{23}$ is identical or different hydrogen, ($C_1$–$C_4$)alkyl, ($C_2$–$C_4$)alkenyl, ($C_2$–$C_4$)alkynyl, ($C_1$–$C_4$)haloalkyl, ($C_2$–$C_4$)haloalkenyl, ($C_1$–$C_4$)alkylcarbamoyl-($C_1$–$C_4$) alkyl, ($C_2$–$C_4$)alkenylcarbamoyl-($C_1$–$C_4$)alkyl, ($C_1$–$C_4$)alkoxy-($C_1$–$C_4$)alkyl, dioxolanyl-($C_1$–$C_4$) alkyl, thiazolyl, furyl, furylalkyl, thienyl, piperidyl, substituted or unsubstituted phenyl, or $R^{22}$ and $R^{23}$ together form a substituted or unsubstituted heterocyclic ring, preferably an oxazolidine, thiazolidine, piperidine, morpholine, hexahydropyrimidine or benzoxazine ring;

or b) one or more compounds from the group consisting of:
1,8-naphthalic anhydride,
methyl diphenylmethoxyacetate,
cyanomethoxyimino(phenyl)acetonitrile (cyometrinil),
1,3-dioxolan-2-ylmethoxyimino(phenyl)acetonitrile (oxabetrinil),
4'-chloro-2,2,2-trifluoroacetophenone O-1,3-dioxolan-2-ylmethyloxime (fluxofenim),
4,6-dichloro-2-phenylpyrimidine (fenclorim),
benzyl-2-chloro-4-trifluoromethyl-1,3-thiazole-5-carboxylate (flurazole),
2-dichloromethyl-2-methyl-1,3-dioxolane (MG-191),
N-(4-methylphenyl)-N'-(1-methyl-1-phenylethyl)urea (dymron),
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea,
1-[4-(N-naphthoylsulfamoyl)phenyl]-3,3-dimethylurea,
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor)

and their salts and esters, preferably ($C_1$–$C_8$);

c) N-acylsulfonamides of the formula (V) and their salts,

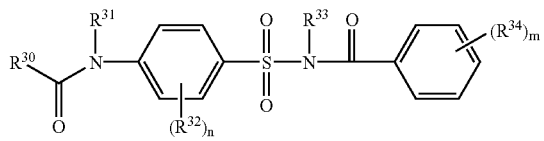 (V)

where $R^{30}$ is hydrogen, a carbon-containing radical such as a hydrocarbon radical, a hydrocarbon oxy radical, a hydrocarbon thio radical or a heterocyclyl radical, each of the last-mentioned 4 radicals being unsubstituted or substituted by one or more identical or different radicals selected from the group consisting of halogen, cyano, nitro, amino, hydroxyl, carboxyl, formyl, carboxamide, sulfonamide and radicals of the formula —$Z^a$—$R^a$, each hydrocarbon moiety preferably having 1 to 20 carbon atoms and a carbon-containing radical $R^{30}$ inclusive of substituents preferably having 1 to 30 carbon atoms;

$R^{31}$ is hydrogen or ($C_1$–$C_4$)alkyl, preferably hydrogen, or $R^{30}$ and $R^{31}$ together with the group of the formula —CO—N— are the radical of a 3- to 8-membered saturated or unsaturated ring;

$R^{32}$ is identical or different halogen, cyano, nitro, amino, hydroxyl, carboxyl, formyl, $CONH_2$, $SO_2NH_2$ or a radical of the formula —$Z^b$—$R^b$;

$R^{33}$ is hydrogen or ($C_1$–$C_4$)alkyl, preferably H;

$R^{34}$ is identical or different halogen, cyano, nitro, amino, hydroxyl, carboxyl, CHO, $CONH_2$, $SO_2NH_2$ or a radical of the formula —$Z^c$—$R^c$;

$R^a$ is a hydrocarbon radical or a heterocyclyl radical, each of the two last-mentioned radicals being unsubstituted or substituted by one or more identical or different radicals selected from the group consisting of halogen, cyano, nitro, amino, hydroxyl, mono- and di-[($C_1$–$C_4$)alkyl]amino, or is an alkyl radical in which more than one, preferably 2 or 3, nonadjacent $CH_2$ groups are each replaced by an oxygen atom;

$R^b$, $R^c$ identical or different are a hydrocarbon radical or a heterocyclyl radical, each of the two last-mentioned radicals being unsubstituted or substituted by one or more identical or different radicals selected from the group consisting of halogen, cyano, nitro, amino, hydroxyl, phosphoryl, halo($C_1$–$C_4$)alkoxy, mono- and di[($C_1$–$C_4$)alkyl]amino, or are an alkyl radical in which more than one, preferably 2 or 3, nonadjacent $CH_2$ groups are each replaced by an oxygen atom;

$Z^a$ is a divalent group of the formula —O—, —S—, —CO—, —CS—, —CO—O—, —CO—S—, —O—CO—, —S—CO—, —SO—, —$SO_2$—, —NR*—, —CO—NR*—, —NR*—CO—, —$SO_2$—NR*— or —NR*—$SO_2$—, the bond shown on the right of the divalent group in question being the bond to the radical $R^a$ and the R* in the last-mentioned 5 radicals independently of one another being in each case H, ($C_1$–$C_4$)alkyl or halo($C_1$–$C_4$)alkyl;

$Z^b$, $Z^c$ independently of one another are a direct bond or a divalent group of the formula —O—, —S—, —CO—, —CS—, —CO—O—, —CO—S—, —O—CO—, —S—CO—, —SO—, —$SO_2$—, —NR*—, —$SO_2$— NR*—, —NR*—$SO_2$—, —CO—NR*— or —NR*—CO—, the bond shown on the right of the divalent group in question being the bond to the radical $R^b$ or $R^c$, respectively, and the R* in the last-mentioned 5 radicals independently of one another being in each case H, ($C_1$–$C_4$)alkyl or halo($C_1$–$C_4$)alkyl;

n is an integer from 0 to 4, preferably 0, 1 or 2, in particular 0 or 1, and m is an integer from 0 to 5, preferably 0, 1, 2 or 3, in particular 0, 1 or 2.

d) Acylsulfamoylbenzamides of the formula (VI), if appropriate in salt form,

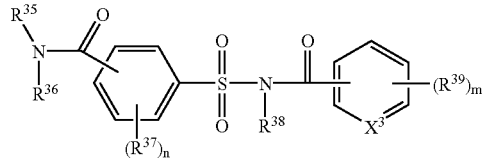 (VI)

where $X^3$ is CH or N;

$R^{35}$ is hydrogen, heterocyclyl or a hydrocarbon radical, the two last-mentioned radicals optionally being substituted by one or more, identical or different radicals selected from the group consisting of halogen, cyano, nitro, amino, hydroxyl, carboxyl, CHO, $CONH_2$, $SO_2NH_2$ and $Z^a$—$R^a$;

$R^{36}$ is hydrogen, hydroxyl, ($C_1$–$C_6$)alkyl, ($C_2$–$C_6$)alkenyl, ($C_2$–$C_6$)alkynyl, ($C_1$–$C_6$)alkoxy, ($C_2$–$C_6$)alkenyloxy, the five last-mentioned radicals optionally being substituted by one or more identical or different radicals selected from the group consisting of halogen, hydroxyl, ($C_1$–$C_4$)alkyl, ($C_1$–$C_4$)alkoxy and ($C_1$–$C_4$) alkylthio, or $R^{35}$ and $R^{36}$ together with the nitrogen atom to which they are attached are a 3- to 8-membered saturated or unsaturated ring;

$R^{37}$ is halogen, cyano, nitro, amino, hydroxyl, carboxyl, CHO, $CONH_2$, $SO_2NH_2$ or $Z^b$—$R^b$;

$R^{38}$ is hydrogen, ($C_1$–$C_4$)alkyl, ($C_2$–$C_4$)alkenyl or ($C_2$–$C_4$)alkynyl;

$R^{39}$ is halogen, cyano, nitro, amino, hydroxyl, carboxyl, phosphoryl, CHO, $CONH_2$, $SO_2NH_2$ or $Z^c$—$R^c$;

$R^a$ is a ($C_2$–$C_{20}$)alkyl radical whose carbon chain is interrupted once or more by oxygen atoms, or is heterocyclyl or a hydrocarbon radical, the two last-mentioned radicals optionally being substituted by one or more, identical or different radicals selected from the group consisting of halogen, cyano, nitro, amino, hydroxyl, mono- and di[($C_1$–$C_4$)alkyl]amino;

$R^b$, $R^c$ identical or different are a ($C_2$–$C_{20}$)alkyl radical whose carbon chain is interrupted once or more by oxygen atoms, or are heterocyclyl or a hydrocarbon radical, the two last-mentioned radicals optionally being substituted by one or more, identical or different radicals selected from the group consisting of halogen, cyano, nitro, amino, hydroxyl, phosphoryl, ($C_1$–$C_4$) haloalkoxy, mono- and di[($C_1$–$C_4$)-alkyl]amino;

$Z^a$ is a divalent unit selected from the group consisting of O, S, CO, CS, C(O)O, C(O)S, SO, $SO_2$, $NR^d$, C(O)$NR^d$ or $SO_2NR^d$;

$Z^b$, $Z^c$ identical or different are a direct bond or a divalent unit selected from the group consisting of O, S, CO, CS, C(O)O, C(O)S, SO, SO$_2$, NR$^d$, SO$_2$NR$^d$ or C(O)NR$^d$;

$R^d$ is hydrogen, (C$_1$–C$_4$)alkyl or (C$_1$–C$_4$)haloalkyl;

n is an integer from 0 to 4, and m in the event that X is CH, is an integer from 0 to 5 and, in the event that X is N, an integer from 0 to 4;

e) compounds of the formula (VII),

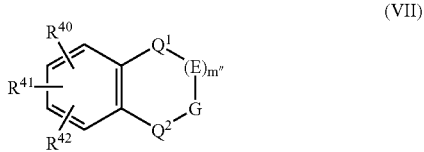

(VII)

where the symbols and indices have the following meanings:

$R^{40}$ is H, (C$_1$–C$_4$)alkyl, (C$_1$–C$_4$)alkyl substituted by (C$_1$–C$_4$)alkyl-X$^4$ or (C$_1$–C$_4$)haloalkyl-X$^4$, (C$_1$–C$_4$)haloalkyl, NO$_2$, CN, —COO—R$^{43}$, NR$_2^{44}$, SO$_2$NR$_2^{45}$ or CONR$_2^{46}$;

$R^{41}$ is H, halogen, (C$_1$–C$_4$)alkyl, CF$_3$, (C$_1$–C$_4$)alkoxy or (C$_1$–C$_4$)haloalkoxy;

$R^{42}$ is H, halogen or (C$_1$–C$_4$)alkyl;

Q$^1$, Q$^2$, E, G are identical or different, —O—, —S—, —CR$_2^{47}$—, —CO—, NR$^{48}$— or a group of the formula (VIII),

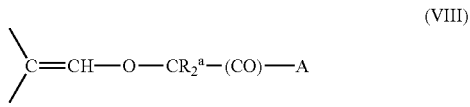

(VIII)

with the proviso that a) at least one of the groups Q$^1$, Q$^2$, E, G is a carbonyl group, that exactly one of this group is a radical of the formula (VIII) and that the group of the formula (VIII) is adjacent to a carbonyl group, and b) two adjacent groups Q$^1$, Q$^2$, E and G cannot simultaneously be oxygen;

$R^a$ is identical or different H or (C$_1$–C$_8$)alkyl or the two radicals $R^a$ together are (C$_2$–C$_6$)alkylene;

A is R$^b$—Y$^3$— or —NR$_2^{49}$;

X$^4$ is —O— or —S(O)$_p$—;

Y$^3$ is —O— or —S—;

$R^b$ is H, (C$_1$–C$_8$)alkyl, (C$_1$–C$_8$)haloalkyl, (C$_1$–C$_4$)alkoxy (C$_1$–C$_8$)alkyl, (C$_3$–C$_6$)alkenyloxy(C$_1$–C$_8$)alkyl, or phenyl(C$_1$–C$_8$)alkyl, the phenyl ring optionally being substituted by halogen, (C$_1$–C$_4$)alkyl, CF$_3$, methoxy or methyl-S(O)$_p$; (C$_3$–C$_6$)alkenyl, (C$_3$–C$_6$)haloalkenyl, phenyl(C$_3$–C$_6$)alkenyl, (C$_3$–C$_6$)alkynyl, phenyl(C$_3$–C$_6$)alkynyl, oxetanyl, furfuryl, tetrahydrofuryl;

$R^{43}$ is H or (C$_1$–C$_4$)alkyl;

$R^{44}$ is identical or different H, (C$_1$–C$_4$)alkyl, (C$_1$–C$_4$) alkylcarbonyl or the two radicals $R^{44}$ together are (C$_4$–C$_5$)alkylene;

$R^{45}$, $R^{46}$ are independently of one another in each case identical or different H, (C$_1$–C$_4$)alkyl, or the two radicals $R^{45}$ and/or $R^{46}$ together are (C$_4$–C$_5$)alkylene, it being possible for one CH$_2$ group to be replaced by O or S or by one or two CH$_2$ groups to be replaced by —NR$^c$—;

$R^c$ is H or (C$_1$–C$_8$)alkyl;

$R^{47}$ is identical or different H, (C$_1$–C$_8$)alkyl or the two radicals $R^{47}$ together are (C$_2$–C$_6$)alkylene;

$R^{48}$ is H, (C$_1$–C$_8$)alkyl, substituted or unsubstituted phenyl, or benzyl which is unsubstituted or substituted on the phenyl ring;

$R^{49}$ is identical or different H, (C$_1$–C$_8$)alkyl, phenyl, phenyl(C$_1$–C$_8$)alkyl, it being possible for a phenyl ring to be substituted by F, Cl, Br, NO$_2$, CN, OCH$_3$, (C$_1$–C$_4$)alkyl or CH$_3$SO$_2$—, or is (C$_1$–C$_4$)alkoxy-(C$_1$–C$_8$)alkyl, (C$_3$–C$_6$)alkenyl, (C$_3$–C$_6$)alkynyl, (C$_3$–C$_6$)cycloalkyl or two radicals $R^{49}$ together are (C$_4$–C$_5$)alkylene, it being possible for one CH$_2$ group to be replaced by O or S or for one or two CH$_2$ groups to be replaced by —NR$^d$—;

$R^d$ is H or (C$_1$–C$_4$)alkyl;

m" is 0 or 1 and p is 0,1 or 2;

inclusive of the stereoisomers and of the salts conventionally used in agriculture.

Herbicidally effective amount means, for the purposes of the invention, an amount of one or more herbicides which is suitable for adversely affecting plant growth.

Antidote-effective amount means, for the purposes of the invention, an amount of one or more safeners which is suitable for at least partially counteracting the phytotoxic effect of a herbicide or herbicide mixture on a useful plant.

Unless specifically defined otherwise, the following definitions generally apply to the radicals in formulae (I) to (VIII) and the subsequent formulae.

The radicals alkyl, alkoxy, haloalkyl, haloalkoxy, alkylamino and alkylthio and the corresponding unsaturated and/or substituted radicals in the carbon skeleton can each be straight-chain or branched.

Alkyl radicals, also in the composite meanings such as alkoxy, haloalkyl and the like, preferably have 1 to 4 carbon atoms and are, for example, methyl, ethyl, n- or i-propyl, n-, i-, t- or 2-butyl. Alkenyl and alkynyl radicals have the meaning of the unsaturated radicals which are possible and which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-in-1-yl, but-3-in-1-yl, 1-methylbut-3-in-1-yl. "(C$_1$–C$_4$)-Alkyl" is the abbreviation for alkyl having 1 to 4 carbon atoms; this also applies analogously to other general definitions of radicals whose ranges of the possible number of carbon atoms is given in brackets.

Cycloalkyl is preferably a cyclic alkyl radical having 3 to 8, preferably 3 to 7, especially preferably 3 to 6, carbon atoms, for example cyclopropyl, cyclobutyl, cyclopentyl and cyclohexyl. Cycloalkenyl and cycloalkynyl denote corresponding unsaturated compounds.

Halogen is fluorine, chlorine, bromine or iodine. Haloalkyl, -alkenyl and -alkynyl are alkyl, alkenyl or alkynyl which are partially or fully substituted by halogen, preferably fluorine, chlorine and/or bromine, in particular by fluorine or chlorine, for example CF$_3$, CHF$_2$, CH$_2$F, CF$_3$CF$_2$, CH$_2$FCHCl, CCl$_3$, CHCl$_2$, CH$_2$CH$_2$Cl. Haloalkoxy is, for example, OCF$_3$, OCHF$_2$, OCH$_2$F, CF$_3$CF$_2$O, OCH$_2$CF$_3$ and OCH$_2$CH$_2$Cl. This also applies analogously to other halogen-substituted radicals.

An aliphatic hydrocarbon radical is, generally, a straight-chain or branched saturated or unsaturated hydrocarbon radical, preferably having 1 to 18, especially preferably 1 to 12, carbon atoms, for example alkyl, alkenyl or alkynyl. Aryl is, generally, a mono-, bi- or polycyclic aromatic system having preferably 6 to 14 carbon atoms, preferably phenyl, naphthyl, tetrahydronaphthyl, indenyl, indanyl, pentalenyl and fluorenyl, especially preferably phenyl.

An aliphatic hydrocarbon radical preferably means alkyl, alkenyl or alkynyl having up to 12 carbon atoms; this also applies analogously to an aliphatic hydrocarbon radical in a hydrocarbonoxy radical.

A heterocyclic ring, heterocyclic radical or heterocyclyl denotes a mono-, bi- or polycyclic ring system which is saturated, unsaturated and/or aromatic and has one or more, preferably 1 to 4, hetero atoms, preferably selected from the group consisting of N, S and O.

Preferred are saturated heterocycles having 3 to 7 ring atoms and one or two hetero atoms selected from the group consisting of N, O and S, chalcogens not being adjacent.

Especially preferred are monocyclic rings having 3 to 7 ring atoms and one hetero atom selected from the group consisting of N, O and S, and also morpholine, dioxolane, piperazine, imidazoline and oxazolidine. Very especially preferred saturated heterocycles are oxirane, pyrrolidone, morpholine and tetrahydrofuran.

Also preferred are partially unsaturated heterocycles having 5 to 7 ring atoms and one or two hetero atoms selected from the group consisting of N, O and S. Especially preferred are partially unsaturated heterocycles having 5 to 6 ring atoms and one hetero atom selected from the group consisting of N, O and S.

Very especially preferred partially unsaturated heterocycles are pyrazoline, imidazoline and isoxazoline.

Also preferred are mono- or bicyclic aromatic heterocycles having 5 to 6 ring atoms which contain one to four hetero atoms selected from the group consisting of N, O, S, chalcogens not being adjacent. Especially preferred are monocyclic aromatic heterocycles having 5 to 6 ring atoms and containing a hetero atom selected from the group consisting of N, O and S, and also pyrimidine, pyrazine, pyridazine, oxazole, thiazole, thiadiazole, oxadiazole, pyrazole, triazole and isoxazole. Very especially preferred are pyrazole, thiazole, triazole and furan.

Substituted radicals such as substituted hydrocarbon radicals, for example substituted alkyl, alkenyl, alkynyl, aryl, phenyl and arylalkyl such as benzyl, or substituted heterocyclyl or heteroaryl, are a substituted radical derived from the unsubstituted skeleton, the substituents preferably being one or more, preferably 1, 2 or 3, in the case of Cl and F also up to the maximum possible number of, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino and alkylsulfinyl, haloalkylsulfinyl, alkylsulfonyl, haloalkylsulfonyl and, in the case of cyclic radicals, also alkyl and haloalkyl, and unsaturated aliphatic radicals corresponding to the above-mentioned saturated hydrocarbon-containing radicals, preferably alkenyl, alkynyl, alkenyloxy, alkynyloxy. In the case of radicals with carbon atoms, those having 1 to 4 carbon atoms, in particular 1 or 2 carbon atoms, are preferred. Preferred are, as a rule, substituents selected from the group consisting of halogen, for example fluorine or chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Especially preferred are the substituents methyl, methoxy and chlorine.

Mono- or disubstituted amino denotes a chemically stable radical selected from the group consisting of the substituted amino radicals which are N-substituted, for example, by one or two identical or different radicals selected from the group consisting of alkyl, alkoxy, acyl and aryl, preferably monoalkylamino, dialkylamino, acylamino, arylamino, N-alkyl-N-arylamino and N-heterocycles. Alkyl radicals having 1 to 4 carbon atoms are preferred. Aryl is preferably phenyl or substituted phenyl. As far as acyl is concerned, the definition given further below applies, preferably $(C_1-C_4)$ alkanoyl. This also applies analogously to substituted hydroxylamino or hydrazino.

Optionally substituted phenyl is, preferably, phenyl which is unsubstituted or mono- or polysubstituted, preferably up to trisubstituted, in the case of halogen such as Cl and F also up to pentasubstituted, by identical or different radicals selected from the group consisting of $(C_1-C_4)$alkyl, $(C_1-C_4)$alkoxy, $(C_1-C_4)$haloalkyl, $(C_1-C_4)$haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

An acyl radical denotes the radical of an organic acid preferably having up to 6 carbon atoms, for example the radical of a carboxylic acid and radicals of acids derived therefrom such as of thiocarboxylic acid, optionally N-substituted iminocarboxylic acids, or the radical of carbonic monoesters, optionally N-substituted carbamic acids, sulfonic acids, sulfinic acids, phosphonic acids, phosphinic acids. Acyl is, for example, formyl, alkylcarbonyl such as $(C_1-C_4$-alkyl$)$carbonyl, phenylcarbonyl, it being possible for the phenyl ring to be substituted, for example as indicated above for phenyl, or alkyloxycarbonyl, phenyloxycarbonyl, benzyloxycarbonyl, alkylsulfonyl, alkylsulfinyl or N-alkyl-1-iminoalkyl.

The formulae (I) to (VIII) also encompass all stereoisomers whose atoms have the same topological linkage, and mixtures of these stereoisomers. Such compounds contain one or more asymmetric carbon atoms or else double bonds which are not especially mentioned in the formulae. The possible stereoisomers which are defined by their specific spatial form, such as enantiomers, diastereomers, Z- and E-isomers, may be obtained by customary methods from stereoisomer mixtures or else be prepared by stereoselective reactions in combination with the use of stereochemically pure starting materials.

Suitable herbicidal active substances according to the invention are those compounds of the formula (I) which, by themselves, cannot be employed, or not optimally employed, in cereal crops and/or maize because they are too harmful for the crop plants.

Herbicides, of the formula (I) are disclosed, for example, in

EP-A 0 496 631, WO-A 97/13 765,
WO-A 97/01 550, WO-A 97/19 087,
WO-A 96/30 368, WO-A 96/31 507,
WO-A 96/26 192, WO-A 96/26 206,
WO-A 96/10 561, WO-A 96/05 183,
WO-A 96/05 198, WO-A 96/05 197,
WO-A 96/05 182, WO-A 97/23 491 and
WO-A 97/27 187.

The cited publications contain extensive information on preparation processes and starting materials. These publications are referred to expressly and they are incorporated herein by reference.

The compounds of the formula (II) are disclosed, for example, in EP-A-0 333 131 (ZA-89/1960), EP-A-0 269 806 (U.S. Pat. No. 4,891,057), EP-A-0 346 620 (AU-A-89/34951), EP-A-0 174 562, EP-A-0 346 620 (WO-A-91/08 202), WO-A-91/07 874 or WO-A 95/07 897 (ZA 94/7120) and in the literature cited therein or can be prepared by or analogously to the processes described therein. The compounds of the formula (III) are disclosed in EP-A-0 086 750, EP-A-0 94349 (U.S. Pat. No. 4,902,340), EP-A-0 191736 (U.S. Pat. No. 4,881,966) and EP-A-0 492 366 and in the literature cited therein or can be prepared by or analogously to the processes described therein. Some compounds are furthermore described in EP-A-0 582 198. The compounds of the formula (II) are disclosed in a large number of patent applications, for example U.S. Pat. No. 4,021,224 and U.S. Pat. No. 4,021,229. Compounds of group (b) are furthermore known from CN-A-87/102 789, EP-A-365484 and from "The Pesticide Manual", The British Crop Protection Council and the Royal Society of Chemistry, 11th edition, Farnham 1997.

The compounds of group (c) are described in WO-A-97/45016, those of group (d) in German Patent Application 197 42 951.3, and those of group (e) in WO-A 98/13 361.

The cited publications contain extensive information on preparation processes and starting materials. These publications are referred to expressly and they are incorporated herein by reference.

Preferred herbicide/safener combinations are those which comprise safeners of the formula (II) and/or (III) in which the symbols and indices have the following meanings:

$R^{24}$ is hydrogen, $(C_1-C_{18})$alkyl, $(C_3-C_{12})$cycloalkyl, $(C_2-C_8)$alkenyl and $(C_2-C_{18})$alkynyl, it being possible for the carbon-containing groups to be substituted by one or more, preferably up to three, radicals $R^{50}$;

$R^{50}$ is identical or different halogen, hydroxyl, $(C_1-C_8)$alkoxy, $(C_1-C_8)$alkylthio, $(C_2-C_8)$alkenylthio, $(C_2-C_8)$alkynylthio, $(C_2-C_8)$alkenyloxy, $(C_2-C_8)$alkynyloxy, $(C_3-C_7)$cycloalkyl, $(C_3-C_7)$cycloalkoxy, cyano, mono- and di$(C_1-C_4)$alkyl)amino, carboxyl, $(C_1-C_8)$alkoxycarbonyl, $(C_2-C_8)$alkenyloxycarbonyl, $(C_1-C_8)$alkylthiocarbonyl, $(C_2-C_8)$alkynyloxycarbonyl, $(C_1-C_8)$alkylcarbonyl, $(C_2-C_8)$alkenylcarbonyl, $(C_2-C_8)$alkynylcarbonyl, 1-(hydroxyimino)$(C_1-C_6)$alkyl, 1-[$(C_1-C_4)$alkylimino]$(C_1-C_4)$alkyl, 1-[$(C_1-C_4)$alkoxyimino]$(C_1-C_6)$alkyl, $(C_1-C_8)$alkylcarbonylamino, $(C_2-C_8)$alkenylcarbonylamino, $(C_2-C_8)$alkynylcarbonylamino, aminocarbonyl, $(C_1-C_8)$alkylaminocarbonyl, di$(C_1-C_6)$alkylaminocarbonyl, $(C_2-C_6)$alkenylaminocarbonyl, $(C_2-C_6)$alkynylaminocarbonyl, $(C_1-C_8)$alkoxycarbonylamino, $(C_1-C_8)$alkylaminocarbonylamino, $(C_1-C_6)$alkylcarbonyloxy, which is unsubstituted or substituted by $R^{51}$, $(C_2-C_6)$alkenylcarbonyloxy, $(C_2-C_6)$alkynylcarbonyloxy, $(C_1-C_8)$alkylsulfonyl, phenyl, phenyl$(C_1-C_6)$alkoxy, phenyl$(C_1-C_6)$alkoxycarbonyl, phenoxy, phenoxy$(C_1-C_6)$alkoxy, phenoxy$(C_1-C_6)$alkoxycarbonyl, phenylcarbonyloxy, phenylcarbonylamino, phenyl$(C_1-C_6)$-alkylcarbonylamino, it being possible for the last-mentioned 9 radicals to be unsubstituted or mono- or polysubstituted in the phenyl ring, preferably up to trisubstituted, by radicals $R^{52}$; $SiR'_3$, $-O-SiR'_3$, $R'_3Si-(C_1-C_8)$alkoxy, $-CO-O-NR'_2$, $-O-N=CR'_2$, $-N=CR'_2$, $-O-NR'_2$, $-NR'_2$, $CH(OR')_2$, $-O-(CH_2)_m-CH(OR')_2$, $-CR'''(OR')_2$, $-O-(CH_2)_mCR'''(OR'')_2$ or by $R''O-CHR'''CHCOR''-(C_1-C_6)$alkoxy, $R^{51}$ is identical or different halogen, nitro, $(C_1-C_4)$alkoxy and phenyl which is unsubstituted or substituted by one or more, preferably up to three, radicals $R^{52}$;

$R^{52}$ is identical or different halogen, $(C_1-C_4)$alkyl, $(C_1-C_4)$alkoxy, $(C_1-C_4)$haloalkyl, $(C_1-C_4)$haloalkoxy or nitro;

R' is identical or different hydrogen, $(C_1-C_4)$alkyl, phenyl which is unsubstituted or substituted by one or more, preferably up to three, radicals $R^{52}$, or two radicals R' together form a $(C_2-C_6)$alkanediyl chain;

R" is identical or different $(C_1-C_4)$alkyl or two radicals R" together form a $(C_2-C_6)$alkanediyl chain;

R''' is hydrogen or $(C_1-C_4)$alkyl;

m is 0, 1, 2, 3, 4, 5 or 6.

Especially preferred are herbicide/safener combinations according to the invention comprising safener of the formula (II) and/or (III) where the symbols and indices have the following meanings:

$R^{24}$ is hydrogen, $(C_1-C_8)$alkyl or $(C_3-C_7)$cycloalkyl, the abovementioned carbon-containing radicals being unsubstituted or mono- or polysubstituted by halogen or mono- or disubstituted, preferably monosubstituted, by radicals $R^{50}$, $R^{50}$ is identical or different hydroxyl, $(C_1-C_4)$alkoxy, carboxyl, $(C_1-C_4)$alkoxycarbonyl, $(C_2-C_6)$alkenyloxycarbonyl, $(C_2-C_6)$alkynyloxycarbonyl, 1-(hydroxyimino)$(C_1-C_4)$alkyl, 1-[$(C_1-C_4)$alkylimino]$(C_1-C_4)$alkyl and 1-[$(C_1-C_4)$alkoxyimino]$(C_{1-C4})$alkyl; $-SiR'_3$, $-O-N=CR'_2$, $-N=CR'_2$, $-NR'_2$, and $-O-NR'_2$, in which R' is identical or different hydrogen, $(C_1-C_4)$alkyl or, as a pair, a $(C_4-C_5)$alkanediyl chain, $R^{27}$, $R^{28}$, $R^{29}$ are identical or different hydrogen, $(C_1-C_8)$alkyl, $(C_1-C_6)$haloalkyl, $(C_3-C_7)$cycloalkyl or phenyl which is unsubstituted or substituted by one or more radicals selected from the group consisting of halogen, cyano, nitro, amino, mono- and di[$(C_1-C_4)$alkyl]amino, $(C_1-C_4)$alkyl, $(C_1-C_4)$haloalkyl, $(C_1-C_4)$alkoxy, $(C_1-C_4)$haloalkoxy, $(C_1-C_4)$alkylthio and $(C_1-C_4)$alkylsulfonyl;

$R^{26}$ is hydrogen, $(C_1-C_8)$alkyl, $(C_1-C_8)$haloalkyl, $(C_1-C_4)$alkoxy)$(C_1-C_4)$alkyl, $(C_1-C_6)$hydroxyalkyl, $(C_3-C_7)$cycloalkyl or tri$(C_1-C_4)$alkylsilyl;

$R^{17}$, $R^{19}$ are identical or different hydrogen, halogen, methyl, ethyl, methoxy, ethoxy, $(C_1$ or $C_2)$haloalkyl, preferably hydrogen, halogen or $(C_1$ or $C_2)$haloalkyl.

Very especially preferred safeners are those in which the symbols and indices in formula (II) have the following meanings:

$R^{17}$ is hydrogen, halogen, nitro or $(C_1-C_4)$haloalkyl;

n' is 1, 2 or 3;

$R^{18}$ is a radical of the formula $OR^{24}$, $R^{24}$ is hydrogen, $(C_1-C_8)$alkyl or $(C_3-C_7)$cycloalkyl, the above carbon-containing radicals being unsubstituted or mono- or polysubstituted, preferably up to trisubstituted, by identical or different halogen radicals or up to disubstituted, preferably monosubstituted by identical or different radicals selected from the group consisting of hydroxyl, $(C_1-C_4)$alkoxy, $(C_1-C_4)$alkoxycarbonyl, $(C_2-C_6)$alkenyloxycarbonyl, $(C_2-C_6)$alkynyloxycarbonyl, 1-(hydroxyimino)$(C_1-C_4)$alkyl, 1-[$(C_1-C_4)$alkylimino]$(C_1-C_4)$alkyl, 1-[$(C_1-C_4)$alkoxyimino]$(C_1-C_4)$alkyl and radicals of the formulae $-SiR'_3$, $-O-N=R'_2$, $-N=CR'_2$, $-NR'_2$ and $-O-NR'_2$, the radicals R' in the abovementioned formulae being identical or different hydrogen, $(C_1–C_4)$alkyl or, in pairs, $(C_4$ or $C_5)$alkanediyl;

$R^{27}$, $R^{28}$, $R^{29}$ are identical or different hydrogen, $(C_1–C_8)$ alkyl, $(C_1–C_6)$haloalkyl, $(C_3–C_7)$cycloalkyl or phenyl which is unsubstituted or substituted by one or more radicals selected from the group consisting of halogen, $(C_1–C_4)$alkyl, $(C_1–C_4)$alkoxy, nitro, $(C_1–C_4)$haloalkyl and $(C_1–C_4)$haloalkoxy, and $R^{26}$ is hydrogen, $(C_1–C_8)$alkyl, $(C_1–C_8)$haloalkyl, $(C_1–C_4)$alkoxy-$(C_1–C_4)$alkyl, $(C_1–C_6)$hydroxyalkyl, $(C_3–C_7)$cycloalkyl or tri$(C_1–C_4)$alkylsilyl.

Very especially preferred safeners are also those of the formula (III) in which the symbols and indices have the following meanings:

$R^{19}$ is hydrogen, halogen or $(C_1–C_4)$haloalkyl;
n' is 1, 2 or 3, where $(R^{19})_{n'}$ is preferably 5-Cl;
$R^{20}$ is a radical of the formula $OR^{24}$;
T is $CH_2$ and
$R^{24}$ is hydrogen, $(C_1–C_8)$alkyl, $(C_1–C_8)$haloalkyl or $(C_1–C_4)$alkoxy$(C_1–C_4)$alkyl, preferably $(C_1–C_8)$alkyl.

Particularly preferred are the safeners of the formula (II) in which the symbols and indices have the following meanings:

W is (W1);
$R^{17}$ is hydrogen, halogen or $(C_1–C_2)$haloalkyl;
n' is 1, 2 or 3, $(R^{17})_{n'}$ preferably being 2,4-$Cl_2$;
$R^{18}$ is a radical of the formula $OR^{24}$;
$R^{24}$ is hydrogen, $(C_1–C_8)$alkyl, $(C_1–C_4)$haloalkyl, $(C_1–C_4)$hydroxyalkyl, $(C_3–C_7)$cycloalkyl, $(C_1–C_4)$ alkoxy$(C_1–C_4)$alkyl or tri$(C_1–C_2)$alkylsilyl, preferably $(C_1–C_4)$alkyl;
$R^{27}$ is hydrogen, $(C_1–C_8)$alkyl, $(C_1–C_4)$haloalkyl or $(C_3–C_7)$cycloalkyl, preferably hydrogen or $(C_1–C_4)$ alkyl, and
$R^{26}$ is hydrogen, $(C_1–C_8)$alkyl, $(C_1–C_4)$haloalkyl, $(C_1–C_4)$hydroxyalkyl, $(C_3–C_7)$cycloalkyl, $(C_1–C_4)$ alkoxy$(C_1–C_4)$alkyl or tri$(C_1–C_2)$alkylsilyl, preferably hydrogen or $(C_1–C_4)$alkyl.

Also particularly preferred are herbicidal compositions comprising a safener of the formula (II) where the symbols and indices have the following meanings:

W is (W2);
$R^{17}$ is hydrogen, halogen or $(C_1–C_2)$haloalkyl;
n' is 1, 2 or 3, $(R^{17})_{n'}$ preferably being 2,4-$Cl_2$;
$R^{18}$ is a radical of the formula $OR^{24}$;
$R^{24}$ is hydrogen, $(C_1–C_8)$alkyl, $(C_1–C_4)$haloalkyl, $(C_1–C_4)$hydroxyalkyl, $(C_3–C_7)$cycloalkyl, $(C_1–C_4)$ alkoxy)-$C_1$-$C_4$-alkyl or tri$(C_1–C_2)$alkylsilyl, preferably $(C_1–C_4)$alkyl, and
$R^{27}$ is hydrogen, $(C_1–C_8)$alkyl, $(C_1–C_4)$haloalkyl, $(C_3–C_7)$cycloalkyl or phenyl, preferably hydrogen or $(C_1–C_4)$alkyl.

Also particularly preferred are safeners of the formula (II) where the symbols and indices have the following meanings:

W is (W3);
$R^{17}$ is hydrogen, halogen or $(C_1–C_2)$haloalkyl;
n' is 1, 2 or 3, $(R^{17})$, preferably being 2,4-$Cl_2$;
$R^{18}$ is a radical of the formula $OR^{24}$;
$R^{24}$ is hydrogen, $(C_1–C_8)$alkyl, $(C_1–C_4)$haloalkyl, $(C_1–C_4)$hydroxyalkyl, $(C_3–C_7)$cycloalkyl, $(C_1–C_4)$ alkoxy$(C_1–C_4)$alkyl or tri$(C_1–C_2)$alkylsilyl, preferably $(C_1–C_4)$alkyl, and
$R^{28}$ is $(C_1–C_8)$alkyl or $(C_1–C_4)$haloalkyl, preferably $C_1$-haloalkyl.

Also particularly preferred are safeners of the formula (II) where the symbols and indices have the following meanings:

W is (W4);
$R^{17}$ is hydrogen, halogen, nitro, $(C_1–C_4)$alkyl, $(C_1–C_2)$ haloalkyl, preferably $CF_3$ or $(C_1–C_4)$alkoxy;
n' is 1, 2 or 3;
m' is 0 or 1;
$R^{18}$ is a radical of the formula $OR^{24}$;
$R^{24}$ is hydrogen, $(C_1–C_4)$alkyl, carboxy$(C_1–C_4)$alkyl, $(C_1–C_4)$alkoxycarbonyl-$(C_1–C_4)$alkyl, preferably $(C_1–C_4)$alkoxy-CO—$CH_2$—, $(C_1–C_4)$alkoxy-CO—C$(CH_3)$H—, HO—CO—$CH_2$— or HO—CO—C$(CH_3)$H—, and
$R^{29}$ is hydrogen, $(C_1–C_4)$alkyl, $(C_1–C_4)$haloalkyl, $(C_3–C_7)$cycloalkyl or phenyl which is unsubstituted or substituted by one or more radicals selected from the group consisting of halogen, $(C_1–C_4)$alkyl, $(C_1–C_4)$ haloalkyl, nitro, cyano and $(C_1–C_4)$alkoxy.

The following groups of compounds are particularly suitable as safeners for the herbicidal active substances of the formula (I):

a) compounds of the dichlorophenylpyrazoline-3-carboxylic acid type (i.e. of the formula (II), where W=W1 and $(R^{17})_{n'}$=2,4-$Cl_2$), preferably compounds such as ethyl 1-(2,4-dichlorophenyl)-5-(ethoxycarbonyl)-5-methyl-2-pyrazoline-3-carboxylate (II-1), and related compounds as they are described in WO-A 91/07874;

b) dichlorophenylpyrazolecarboxylic acid derivatives (i.e. of the formula (II), where W=(W2) and $(R^{17})_{n'}$=2,4-$Cl_2$), preferably compounds such as ethyl 1-(2,4-dichlorophenyl)-5-methylpyrazole-3-carboxylate (II-2), ethyl 1-(2,4-dichlorophenyl)-5-isopropylpyrazole-3-carboxylate (II-3), ethyl 1-(2,4-dichlorophenyl)-5-(1,1-dimethylethyl)pyrazole-3-carboxylate (II-4), ethyl 1-(2,4-dichlorophenyl)-5-phenylpyrazole-3-carboxylate (II-5) and related compounds as they are described in EP-A-0 333 131 and EP-A-0 269 806.

c) Compounds of the triazolecarboxylic acid type (i.e. of the formula (II), where W=(W3) and $(R^{17})_{n'}$=2,4-$Cl_2$), preferably compounds such as fenchlorazol, i.e. ethyl 1-(2,4-dichlorophenyl)-5-trichloromethyl-(1H)-1,2,4-triazole-3-carboxylate (II-6), and related compounds (see EP-A-0 174 562 and EP-A-0 346 620);

d) compounds of the 5-benzyl- or 5-phenyl-2-isoxazoline-3-carboxylic acid type or the 5,5-diphenyl-2-isoxazoline-3-carboxylic acid type (where W=(W4)), preferably compounds such as ethyl 5-(2,4-dichlorobenzyl)-2-isoxazoline-3-carboxylate (II-7) or ethyl 5-phenyl-2-isoxazoline-3-carboxylate (II-8) and related compounds as they are described in WO-A-91/08202, or of the ethyl 5,5-diphenyl-2-isoxazolinecarboxylate type (II-9), the n-propyl 5,5-diphenyl-2-isoxazolinecarboxylate type (II-10) or the ethyl 5-(4-fluorophenyl)-5-phenyl-2-isoxazoline-3-carboxylate type (II-11), as they are described in WO-A-95/07897.

e) Compounds of the 8-quinolinoxyacetic acid type, for example those of the formula (III), where $(R^{19})_{n'}$=5-Cl, hydrogen, $R^{20}$=$OR^{24}$ and T=$CH_2$, preferably the compounds 1-methylhexyl(5-chloro-8-quinolinoxy)acetate (III-1, cloquintocet), 1,3-dimethylbut-1-yl(5-chloro-8-quinolinoxy)acetate (III-2), 4-allyloxy-butyl(5-chloro-8-quinolinoxy)acetate (III-3), 1-allyloxyprop-2-yl(5-chloro-8-quinolinoxy)acetate (III-4), ethyl(5-chloro-8-quinolinoxy)acetate (III-5), methyl(5-chloro-8-quinolinoxy)acetate (III-6), allyl(5-chloro-8-quinolinoxy)acetate (III-7), 2-(2-propylideneiminoxy)-1-ethyl(5-chloro-8-quinolinoxy)acetate (III-8), 2-oxoprop-1-yl(5-chloro-8-quinolinoxy)acetate (III-9)

and related compounds as they are described in EP-A-0 860 750, EP-A-0 094 349 and EP-A-0 191 736 or EP-A-0 492 366.
  f) Compounds of the (5-chloro-8-quinolinoxy)malonic acid type, i.e. of the formula (III), where $(R^{17})_n$=5-Cl, $R^{20}$=$OR^{24}$, T=—CH(COO-alkyl)-, preferably the compounds diethyl (5-chloro-8-quinolinoxy)malonate, diallyl (5-chloro-8-quinolinoxy)malonate, methyl ethyl (5-chloro-8-quinolinoxy)malonate and related compounds as they are described in EP-A-0 582 198.
  g) compounds of the dichloroacetamide type, i.e. of the formula (IV), preferably:
N,N-diallyl-2,2-dichloroacetamide (dichlormid, disclosed in U.S. Pat. No. 4,137,070),
4-dichloroacetyl-3,4-dihydro-3-methyl-2H-1,4-benzoxazine (benoxacor, disclosed in EP 0 149 974),
$N^1$,$N^2$-diallyl-$N^2$-dichloroacetylglycinamide (DKA-24, disclosed in HU 2143821),
4-dichloroacetyl-1-oxa-4-aza-spiro[4,5]decane (AD-67),
2,2-dichloro-N-(1,3-dioxolan-2-ylmethyl)-N-(2-propenyl)acetamide (PPG-1292),
3-dichloroacetyl-2,2,5-trimethyloxazolidine,
3-dichloroacetyl-2,2-dimethyl-5-phenyloxazolidine,
3-dichloroacetyl-2,2-dimethyl-5-(2-thienyl)oxazolidine,
3-dichloroacetyl-5-(2-furanyl)-2,2-dimethyloxazolidine (furilazole, MON 13900),
1-dichloroacetylhexahydro-3,3,8a-trimethylpyrrolo[1,2-a]pyrimidine-6(2H)-one (dicyclonon, BAS 145138),
  h) compounds of group B(b), preferably
1,8-naphthalic anhydride,
methyl diphenylmethoxyacetate,
cyanomethoxyimino(phenyl)acetonitrile (cyometrinil),
1,3-dioxolan-2-ylmethoxyimino(phenyl)acetonitrile (oxabetrinil),
4'-chloro-2,2,2-trifluoroacetophenone O-1,3-dioxolan-2-ylmethyloxime (fluxofenim),
4,6-dichloro-2-phenylpyrimidine (fenclorim),
benzyl 2-chloro-4-trifluoromethyl-1,3-thiazole-5-carboxylate (flurazole),
2-dichloromethyl-2-methyl-1,3-dioxolan (MG-191),
N-(4-methylphenyl)-N'-(1-methyl-1-phenylethyl)urea (dymron),
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea,
1-[4-(N-naphthoylsulfamoyl)phenyl]-3,3-dimethylurea,
(2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor)

and their salts and esters, preferably $(C_1–C_8)$.

Furthermore preferred as safeners are compounds of the formula (V) or their salts, where
$R^{30}$ is hydrogen, $(C_1–C_6)$alkyl, $(C_3–C_6)$cycloalkyl, furanyl or thienyl, it being possible for each of the last-mentioned 4 radicals to be unsubstituted or substituted by one or more substituents selected from the group consisting of halogen, $(C_1–C_4)$alkoxy, halo$(C_1–C_6)$alkoxy and $(C_1–C_4)$alkylthio and, in the case of cyclic radicals, also $(C_1–C_4)$alkyl and $(C_1–C_4)$haloalkyl,
$R^{31}$ is hydrogen,
$R^{32}$ is halogen, halo$(C_1–C_4)$alkyl, halo$(C_1–C_4)$alkoxy, $(C_1–C_4)$alkyl, $(C_1–C_4)$alkoxy, $(C_1–C_4)$alkylsulfonyl, $(C_1–C_4)$alkoxycarbonyl or $(C_1–C_4)$alkylcarbonyl, preferably halogen, $(C_1–C_4)$haloalkyl, such as trifluoromethyl, $(C_1–C_4)$alkoxy, halo$(C_1–C_4)$alkoxy, $(C_1–C_4)$alkoxycarbonyl or $(C_1–C_4)$alkylsulfonyl,
$R^{33}$ is hydrogen,
$R^{34}$ is halogen, $(C_1–C_4)$alkyl, halo$(C_1–C_4)$alkyl, halo$(C_1–C_4)$alkoxy, $(C_3–C_6)$cycloalkyl, phenyl, $(C_1–C_4)$alkoxy, cyano, $(C_1–C_4)$alkylthio, $(C_1–C_4)$alkylsulfinyl, $(C_1–C_4)$alkylsulfonyl, $(C_1–C_4)$alkoxycarbonyl or $(C_1–C_4)$alkylcarbonyl, preferably halogen, $(C_1–C_4)$alkyl, $(C_1–C_4)$haloalkyl, such as trifluoromethyl, halo $(C_1–C_4)$alkoxy, $(C_1–C_4)$alkoxy or $(C_1–C_4)$alkylthio,
n is 0, 1 or 2 and
m is 1 or 2.

Furthermore preferred are safeners of the formula (VI), in which
$X^3$ is CH;
$R^{35}$ is hydrogen, $(C_1–C_6)$alkyl, $(C_3–C_6)$cycloalkyl, $(C_2–C_6)$alkenyl, $(C_5–C_6)$cycloalkenyl, phenyl or 3- to 6-membered heterocyclyl having up to three hetero atoms selected from the group consisting of nitrogen, oxygen and sulfur, it being possible for the six last-mentioned radicals to be optionally substituted by one or more identical or different substituents selected from the group consisting of halogen, $(C_1–C_6)$alkoxy, $(C_1–C_6)$haloalkoxy, $(C_1–C_2)$alkylsulfinyl, $(C_1–C_2)$alkylsulfonyl, $(C_3–C_6)$cycloalkyl, $(C_1–C_4)$alkoxycarbonyl, $(C_1–C_4)$alkylcarbonyl and phenyl and, in the case of cyclic radicals, also $(C_1–C_4)$alkyl and $(C_1–C_4)$haloalkyl;
$R^{36}$ is hydrogen, $(C_1–C_6)$alkyl, $(C_2–C_6)$alkenyl, $(C_2–C_6)$alkynyl, it being possible for the three last-mentioned radicals optionally to be substituted by one or more, identical or different substituents selected from the group consisting of halogen, hydroxyl, $(C_1–C_4)$alkyl, $(C_1–C_4)$alkoxy and $(C_1–C_4)$alkylthio;
$R^{37}$ is halogen, $(C_1–C_4)$haloalkyl, $(C_1–C_4)$haloalkoxy, nitro, $(C_1–C_4)$alkyl, $(C_1–C_4)$alkoxy, $(C_1–C_4)$alkylsulfonyl, $(C_1–C_4)$alkoxycarbonyl or $(C_1–C_4)$alkylcarbonyl;
$R^{38}$ is hydrogen;
$R^{39}$ is halogen, nitro, $(C_1–C_4)$alkyl, $(C_1–C_4)$haloalkyl, $(C_1–C_4)$haloalkoxy, $(C_3–C_6)$cycloalkyl, phenyl, $(C_1–C_4)$alkoxy, cyano, $(C_1–C_4)$alkylthio, $(C_1–C_4)$alkylsulfinyl, $(C_1–C_4)$alkylsulfonyl, $(C_1–C_4)$alkoxycarbonyl or $(C_1–C_4)$alkylcarbonyl;
n is 0, 1 or 2 and
m is 1 or 2.

Especially preferred amongst the safeners of the formula (VII) are the sub-groups which follow:
  compounds in which $R^{48}$ and $R^{49}$ are H, $(C_1–C_8)$alkyl, phenyl, phenyl$(C_1–C_8)$alkyl, $(C_1–C_4)$alkoxy-$(C_1–C_8)$alkyl, $(C_3–C_6)$alkenyl or $(C_3–C_6)$alkynyl, it being possible for phenyl rings to be substituted by F, Cl, Br, $NO_2$, CN, $OCH_3$, $(C_1–C_4)$alkyl or $CH_3$—$SO_2$—;
  compounds in which $R^a$ is H;
  compounds in which A is $R^b$—$Y^3$;
  compounds in which E is O;
  compounds in which $Q^1$ is $CR_2^{47}$;
  compounds in which $R^{47}$ is H;
  compounds in which m" is 1 and E is O or S;
  compounds in which m"=0;

compounds in which $R^{40}$ to $R^{44}$ are H, m" is 1, E is O, $Q^1$ is $CR_2^{47}$ and A is $R^b$—$Y^3$, in particular those where $R^{47}$ is H, $R^b$ is $CH_3$ and $Y^3$ is O;

compounds in which $Q^1$ is $CR_2^{47}$ and m equals 0, in particular those in which $R^{44}$ and $R^{47}$ are H and A is $R^b$—$Y^3$ where $R^b$ is preferably methyl and $Y^3$ is preferably O.

Preferred groups of herbicides of the formula (I) are listed in Tables 1 to 16 which follow.

TABLE 1

(V = V1, Z = Z1):

| Ex. | R | R1 | (R9)q | R10 |
|---|---|---|---|---|
| 1-1 | H | c-Pr | 4-SEt | 2-Bzl |
| 1-2 | H | c-Pr | 4-SMe | 2-Bzl |
| 1-3 | H | c-Pr | 4-F-3-Me | 2-(4-Cl-Bzl) |
| 1-4 | H | c-Pr | 4-SMe | 2-(2-Me-Bzl) |
| 1-5 | H | c-Pr | 4-SO₂Me | 2-(2-Cl-Bzl) |
| 1-6 | H | c-Pr | 4-SO₂Me | 2-(3-Cl-Bzl) |
| 1-7 | H | c-Pr | 4-SO₂Me | 2-(4-Cl-Bzl) |
| 1-8 | H | c-Pr | 4-SO₂Me | 2-(1-triazolyl) |
| 1-9 | COOEt | c-Pr | 4-SO₂Me | 2-(1-triazolyl) |
| 1-10 | COOMe | c-Pr | 4-SO₂Me | 2-(1-triazolyl) |
| 1-11 | H | c-Pr | 4-SO₂Me | 2-(1-pyrazolyl) |
| 1-12 | COOEt | c-Pr | 4-SO₂Me | 2-(1-pyrazolyl) |
| 1-13 | COOMe | c-Pr | 4-SO₂Me | 2-(1-pyrazolyl) |
| 1-14 | H | c-Pr | 4-SO₂Me | 2-(3,5-DiMe-1-pyrazolyl) |
| 1-15 | COOEt | c-Pr | 4-SO₂Me | 2-(3,5-DiMe-1-pyrazolyl) |
| 1-16 | COOMe | c-Pr | 4-SO₂Me | 2-(3,5-DiMe-1-pyrazolyl) |
| 1-17 | H | 1-Me-c-Pr | 4-SO₂Me | 2-(1-triazolyl) |
| 1-18 | COOEt | 1-Me-c-Pr | 4-SO₂Me | 2-(1-pyrazolyl) |
| 1-19 | COOMe | 1-Me-c-Pr | 4-SO₂Me | 2-(3,5-DiMe-1-pyrazolyl) |
| 1-20 | H | c-Pr | 2-Cl-4-SO₂Me | 3-(1-triazolyl) |
| 1-21 | COOEt | c-Pr | 4-CF₃ | 2-(CH2-1-triazolyl) |
| 1-22 | H | c-Pr | 4-CF₃ | 2-[CH2—PO(OEt)2] |
| 1-23 | H | c-Pr | 4-CF₃ | 2-[CH2—PO(OMe)2] |
| 1-24 | H | c-Pr | 3-Br | 2-[CH2—PO(OMe)2] |
| 1-25 | COOEt | c-Pr | 4-Br | 2-[CH2—PO(OEt)2] |
| 1-26 | COOEt | c-Pr | 3,4-DiCl | 2-[CH2—PO(OMe)2] |
| 1-27 | COOEt | c-Pr | 4-Br | 2-[CH2—PO(OMe)2] |
| 1-28 | COOEt | c-Pr | 4-CF₃ | 2-[CH2—PO(OMe)2] |
| 1-29 | H | C—Pr | 2-Cl-4-SO₂Me | 3-(2-thiazolyl) |
| 1-30 | COOEt | C—Pr | 2-Cl-4-SO₂Me | 3-(2-thiazolyl) |
| 1-31 | H | 1-Me-c-Pr | 2-Cl-4-SO₂Me | 3-(2-thiazolyl) |
| 1-32 | COOEt | 1-Me-c-Pr | 2-Cl-4-SO₂Me | 3-(2-thiazolyl) |
| 1-33 | H | c-Pr | — | 4-SF₅ |

TABLE 2

(V = V2, Z = Z1):

| Ex. | R2 | R3 | R4 | (R9)q | R10 |
|---|---|---|---|---|---|
| 2-1 | H | H | Me | 2-Cl-4-SO₂Me | 3-(2-thiazolyl) |
| 2-2 | Me | H | Me | 2-Cl-4-SO₂Me | 3-(2-thiazolyl) |
| 2-3 | H | SO₂Me | Me | 2-Cl-4-SO₂Me | 3-(2-thiazolyl) |
| 2-4 | H | SO₂-(4-Me—Ph) | Me | 2-Cl-4-SO₂Me | 3-(2-thiazolyl) |

TABLE 3

(V = V3, Z = Z1):

| Ex. | (R5)o | R6 | (R9)q | R10 |
|---|---|---|---|---|
| 3-1 | — | OH | 2-Cl-4-SO₂Me | 3-(2-thiazolyl) |
| 3-2 | 5-(CH(OMe)₂) | OH | 2-Cl-4-SO₂Me | 3-(2-thiazotyl) |
| 3-3 | — | OH | 4-Cl-2-SO₂Me | 3-(2-thiazolyl) |
| 3-4 | 5-(CH(OMe)₂) | OH | 4-Cl-2-SO₂Me | 3-(2-thiazolyl) |
| 3-5 | 5,5-DiMe | OH | 2-Me-4-SO₂Me | 3-(2-furanyl) |
| 3-6 | 5,5-DiMe | OH | 2-Cl-4-SO₂Me | 3-(2-furanyl) |
| 3-7 | — | OH | 2-Me-4-SO₂Me | 3-(2-furanyl) |
| 3-8 | — | OH | 2-Cl-4-SO₂Me | 3-(2-furanyl) |
| 3-9 | — | OH | 2-Cl-4-SO₂Me | 3-CH2OMe |
| 3-10 | — | OH | 2-Cl-4-SO₂Me | 3-[CH2—CH(OMe)2] |
| 3-11 | — | OH | 2-Cl-4-SO₂Me | 3-O-C2H4-OMe |
| 3-12 | — | OH | 2,4-DiCl | 3-O—CH2-(1,3-dioxolan-4-yl) |
| 3-13 | — | OH | 2-Cl-4-SO₂Me | 3-(2-isoxazolin-3-yl) |
| 3-14 | — | OH | 2-Cl-4-SO₂Me | 3-(1-pyrazolylmethyl) |
| 3-15 | — | OH | 2-Cl-4-SO₂Me | 3-morpholinyl |

TABLE 4

(V = V4, Z = Z1):

| Ex. | R7 | R8 | (R9)q | R10 |
|---|---|---|---|---|
| 4-1 | c-Pr | CN | 4-S—Et | 2-Bzl |
| 4-2 | c-Pr | CN | 4-S—Me | 2-Bzl |
| 4-3 | c-Pr | CN | 4-F-3-Me | 2-(4-Cl-Bzl) |
| 4-4 | c-Pr | CN | 4-S—Me | 2-(2-Me-Bzl) |
| 4-5 | c-Pr | CN | 4-SO₂Me | 2-(2-Cl-Bzl) |
| 4-6 | c-Pr | CN | 4-SO₂Me | 2-(3-Cl-Bzl) |
| 4-7 | c-Pr | CN | 4-SO₂Me | 2-(4-Cl-Bzl) |
| 4-8 | c-Pr | CN | 4-Br | 2-(1-pyrazolyl) |
| 4-9 | c-Pr | CN | 3,4-DiCl | 2-(CH2-1-triazolyl) |
| 4-10 | c-Pr | CN | 4-Br | 2-[CH2PO(OEt)2] |
| 4-11 | c-Pr | CN | 4-Br | 2-[CH2PO(OMe)2] |
| 4-12 | c-Pr | CN | — | 2-[CH2PO(OEt)2] |
| 4-13 | c-Pr | CN | — | 2-[CH2PO(OMe)2] |
| 4-14 | c-Pr | CN | 2-Cl-4-SO₂Me | 3-(2-thiazolyl) |
| 4-15 | 1-Me-c-Pr | CN | 2-Cl-4-SO₂Me | 3-(2-thiazolyl) |
| 4-16 | t-Bu | CN | 2-Cl-4-SO₂Me | 3-(2-thiazolyl) |

TABLE 5

(V = V1, Z = Z2)

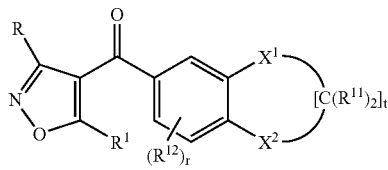

| Ex. | R | R1 | X$^1$ | X$^2$ | [C(R11)2]$_t$ | (R12)$_r$ |
|---|---|---|---|---|---|---|
| 5-1 | H | c-Pr | C(OC$_2$H$_4$O) | SO$_2$ | C$_2$H$_4$ | 2,5-DiMe |
| 5-2 | H | c-Pr | CHOMe | SO$_2$ | C$_2$H$_4$ | 2-Me-5-Cl |
| 5-3 | H | c-Pr | O | O | CF$_2$ | 2-[CH$_2$PO(OMe)$_2$] |
| 5-4 | COOEt | c-Pr | O | O | CF$_2$ | 2-[CHCH$_3$PO(OEt)$_2$] |
| 5-5 | COOEt | 1-Me-c-Pr | O | O | CF$_2$ | 2-[CH$_2$PO(OMe)$_2$] |
| 5-6 | COOEt | c-Pr | O | O | CF$_2$ | 2-[CHCH$_3$PO(OMe)$_2$] |
| 5-7 | H | c-Pr | C(SC$_2$H$_4$S) | SO$_2$ | C$_2$H$_4$ | 2,5-DiMe |
| 5-8 | H | c-Pr | C(SC$_2$H$_4$S) | SO$_2$ | C$_2$H$_4$ | 2-Me-5-Cl |
| 5-9 | H | c-Pr | C(CH$_3$)$_2$ | SO$_2$ | C$_2$H$_4$ | 2,5-DiMe |
| 5-10 | H | c-Pr | CHOMe | SO$_2$ | C$_2$H$_4$ | 2,5-DiMe |
| 5-11 | H | c-Pr | CHOC$_2$H$_4$F | SO$_2$ | C$_2$H$_4$ | 2,5-DiMe |
| 5-12 | H | c-Pr | C=NOMe | SO$_2$ | C$_2$H$_4$ | 2,5-DiMe |
| 5-13 | H | c-Pr | C=NOMe | SO$_2$ | C$_2$H$_4$ | 2-Me |
| 5-14 | H | c-Pr | C=NOMe | S | C$_2$H$_4$ | 2,5-DiMe |

TABLE 6

(V = V2, Z = Z2):

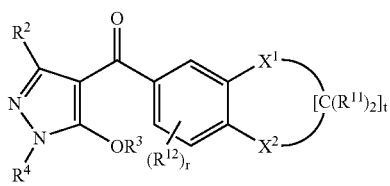

| Ex. | R2 | R3 | R4 | X$^1$ | X$^2$ | [C(R11)2]$_t$ | (R12)$_r$ |
|---|---|---|---|---|---|---|---|
| 6-1 | H | H | Et | C(OC$_2$H$_4$O) | SO$_2$ | C$_2$H$_4$ | 2,5-DiMe |
| 6-2 | H | H | Et | CHOMe | SO$_2$ | C$_2$H$_4$ | 2-Me-5-Cl |
| 6-3 | H | H | Me | C(OC$_2$H$_4$O) | SO$_2$ | C$_2$H$_4$ | 2,5-DiMe |
| 6-4 | H | H | Me | CHOMe | SO$_2$ | C$_2$H$_4$ | 2-Me-5-Cl |
| 6-5 | H | H | Et | CO | SO$_2$ | C$_2$H$_4$ | 2,5-DiMe |
| 6-6 | H | H | Et | CO | SO$_2$ | C$_2$H$_4$ | 2-Me-5-Cl |
| 6-7 | H | SO$_2$Me | Et | C(OC$_2$H$_4$O) | SO$_2$ | C$_2$H$_4$ | 2,5-DiMe |
| 6-8 | H | SO$_2$Me | Et | CHOMe | SO$_2$ | C$_2$H$_4$ | 2-Me-5-Cl |
| 6-9 | H | SO$_2$Me | Me | C(OC$_2$H$_4$O) | SO$_2$ | C$_2$H$_4$ | 2,5-DiMe |
| 6-10 | H | SO$_2$Me | Me | CHOMe | SO$_2$ | C$_2$H$_4$ | 2-Me-5-Cl |
| 6-11 | H | SO$_2$Me | Et | CO | SO$_2$ | C$_2$H$_4$ | 2,5-DiMe |
| 6-12 | H | SO$_2$Me | Et | CO | SO$_2$ | C$_2$H$_4$ | 2-Me-5-Cl |
| 6-13 | Me | SO$_2$-(4-Me—Ph) | Me | C=NOMe | SO$_2$ | C$_2$H$_4$ | 2,5-DiMe |
| 6-14 | Me | CH$_2$—CO—Ph | Me | C=NOMe | SO$_2$ | C$_2$H$_4$ | 2,5-DiMe |

TABLE 7

(V = V3, Z = Z2)

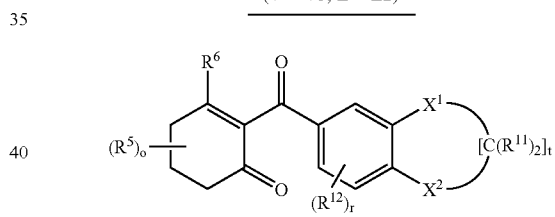

| Ex. | R5 | R6 | X$^1$ | X$^2$ | [C(R11)2]$_t$ | (R12)$_r$ |
|---|---|---|---|---|---|---|
| 7-1 | — | OH | C(OC$_2$H$_4$O) | SO$_2$ | C$_2$H$_4$ | 2,5-DiMe |
| 7-2 | — | OH | CHOMe | SO$_2$ | C$_2$H$_4$ | 2-Me-5-Cl |
| 7-3 | 4,4-DiMe | OH | C(OC$_2$H$_4$O) | SO$_2$ | C$_2$H$_4$ | 2,5-DiMe |
| 7-4 | 4,4-DiMe | OH | CHOMe | SO$_2$ | C$_2$H$_4$ | 2-Me-5-Cl |
| 7-5 | — | OH | C(OC$_2$H$_4$O) | SO$_2$ | C$_2$H$_4$ | — |
| 7-6 | — | OH | CHOMe | SO$_2$ | C$_2$H$_4$ | — |
| 7-7 | — | OH | CO | SO$_2$ | C$_2$H$_4$ | 2,5-DiMe |
| 7-8 | — | OH | CO | SO$_2$ | C$_2$H$_4$ | 2-Me-5-Cl |
| 7-9 | — | OH | C(OC$_2$H$_4$O) | SO$_2$ | C$_2$H$_4$ | 2,5-DiCl |
| 7-10 | — | OH | C(SC$_2$H$_4$S) | SO$_2$ | C$_2$H$_4$ | 2,5-DiMe |
| 7-11 | 5-(CH(OMe)2) | OH | C(OC$_2$H$_4$O) | SO$_2$ | C$_2$H$_4$ | 2,5-DiMe |
| 7-12 | 5-(CH(OMe)2) | OH | CHOMe | SO$_2$ | C$_2$H$_4$ | 2,5-DiMe |
| 7-13 | — | OH | C=NOH | SO$_2$ | C$_2$H$_4$ | — |
| 7-14 | — | OH | CHOMe | SO$_2$ | C$_2$H$_4$ | 2,5-DiMe |

TABLE 8

(V = V4, Z = Z2):

| Ex. | R7 | R8 | X¹ | X² | [C(R11)2]t | (R12)r |
|---|---|---|---|---|---|---|
| 8-1 | c-Pr | CN | C(OC$_2$H$_4$O) | SO$_2$ | C$_2$H$_4$ | 2,5-DiMe |
| 8-2 | c-Pr | CN | CHOMe | SO$_2$ | C$_2$H$_4$ | 2-Me-5-Cl |
| 8-3 | 1-Me-c-Pr | CN | C(OC$_2$H$_4$O) | SO$_2$ | C$_2$H$_4$ | 2,5-DiMe |
| 8-4 | 1-Me-c-Pr | CN | CHOMe | SO$_2$ | C$_2$H$_4$ | 2-Me-5-Cl |
| 8-5 | c-Pr | CN | C(SC$_2$H$_4$S) | SO$_2$ | C$_2$H$_4$ | 2,5-DiMe |
| 8-6 | c-Pr | CN | C(SC$_2$H$_4$S) | SO$_2$ | C$_2$H$_4$ | 2-Me-5-Cl |
| 8-7 | c-Pr | CN | C(CH$_3$)$_2$ | SO$_2$ | C$_2$H$_4$ | 2,5-DiMe |
| 8-8 | c-Pr | CN | CHOMe | SO$_2$ | C$_2$H$_4$ | 2,5-DiMe |
| 8-9 | c-Pr | CN | CHOC$_2$H$_4$F | SO$_2$ | C$_2$H$_4$ | 2,5-DiMe |
| 8-10 | c-Pr | CN | C=NOMe | SO$_2$ | C$_2$H$_4$ | 2,5-DiMe |
| 8-11 | c-Pr | CN | C=NOMe | SO$_2$ | C$_2$H$_4$ | 2-Me |
| 8-12 | c-Pr | CN | C=NOMe | S | C$_2$H$_4$ | 2,5-DiMe |

TABLE 9

(V = V1, Z = Z3):

| Ex. | R | R1 | Y1 | Y2 | (R12)r | R13 |
|---|---|---|---|---|---|---|
| 9-1 | H | c-Pr | SO$_2$ | CO | — | Me |
| 9-2 | H | c-Pr | SO$_2$ | CO | — | H |
| 9-3 | COOEt | c-Pr | SO$_2$ | CO | — | Me |
| 9-4 | COOEt | c-Pr | SO$_2$ | CO | — | H |
| 9-5 | H | 1-Me-c-Pr | SO$_2$ | CO | — | Me |
| 9-6 | H | 1-Me-c-Pr | SO$_2$ | CO | — | H |
| 9-7 | COOEt | 1-Me-c-Pr | SO$_2$ | CO | — | Me |
| 9-8 | COOEt | 1-Me-c-Pr | SO$_2$ | CO | — | H |
| 9-9 | H | 1-SMe-c-Pr | SO$_2$ | CO | — | Me |
| 9-10 | H | 1-SMe-c-Pr | SO$_2$ | CO | — | H |
| 9-11 | COOEt | 1-SMe-c-Pr | SO$_2$ | CO | — | Me |
| 9-12 | COOEt | 1-SMe-c-Pr | SO$_2$ | CO | — | H |
| 9-13 | H | c-Pr | CO | SO$_2$ | — | Me |
| 9-14 | COOEt | c-Pr | CO | SO$_2$ | — | Me |
| 9-15 | H | 1-Me-c-Pr | CO | SO$_2$ | — | Me |
| 9-16 | COOEt | 1-Me-c-Pr | CO | SO$_2$ | — | Me |
| 9-17 | H | 1-SMe-c-Pr | CO | SO$_2$ | — | Me |
| 9-18 | COOEt | 1-SMe-c-Pr | CO | SO$_2$ | — | Me |

TABLE 10

(V = V2, Z = Z3):

| Ex. | R2 | R3 | R4 | Y1 | Y2 | (R12)r | R13 |
|---|---|---|---|---|---|---|---|
| 10-1 | H | H | Et | SO$_2$ | CO | — | Me |
| 10-2 | H | H | Et | SO$_2$ | CO | — | H |
| 10-3 | Me | H | Et | SO$_2$ | CO | — | Me |
| 10-4 | Me | H | Et | SO$_2$ | CO | — | H |
| 10-5 | H | H | Me | SO$_2$ | CO | — | Me |
| 10-6 | H | H | Me | SO$_2$ | CO | — | H |
| 10-7 | Me | H | Me | SO$_2$ | CO | — | Me |
| 10-8 | Me | H | Me | SO$_2$ | CO | — | H |
| 10-9 | H | H | Me | CO | SO$_2$ | — | Me |
| 10-10 | H | H | Me | CO | SO$_2$ | — | H |
| 10-11 | Me | H | Me | CO | SO$_2$ | — | Me |
| 10-12 | Me | H | Me | CO | SO$_2$ | — | H |
| 10-13 | Me | H | Me | CO | SO$_2$ | 2-Me | Me |

TABLE 11

(V = V3, Z = Z3):

| Ex. | (R5)o | R6 | Y1 | Y2 | (R12)r | R13 |
|---|---|---|---|---|---|---|
| 11-1 | — | OH | SO$_2$ | CO | — | Me |
| 11-2 | — | OH | SO$_2$ | CO | — | H |
| 11-3 | 4,4-DiMe | OH | SO$_2$ | CO | — | Me |
| 11-4 | 4,4-DiMe | OH | SO$_2$ | CO | — | H |
| 11-5 | — | OH | CO | SO$_2$ | — | Me |
| 11-6 | — | OH | CO | SO$_2$ | — | H |
| 11-7 | 4,4-DiMe | OH | CO | SO$_2$ | — | Me |
| 11-8 | 4,4-DiMe | OH | CO | SO$_2$ | — | H |

TABLE 12

(V = V4, Z = Z3):

| Ex. | R7 | R8 | Y1 | Y2 | (R12)r | R13 |
|---|---|---|---|---|---|---|
| 12-1 | c-Pr | CN | SO$_2$ | CO | — | Me |
| 12-2 | c-Pr | CN | SO$_2$ | CO | — | H |
| 12-3 | 1-Me-c-Pr | CN | SO$_2$ | CO | — | Me |
| 12-4 | 1-Me-c-Pr | CN | SO$_2$ | CO | — | H |
| 12-5 | c-Pr | CN | CO | SO$_2$ | — | Me |
| 12-6 | c-Pr | CN | CO | SO$_2$ | — | H |
| 12-7 | 1-Me-c-Pr | CN | CO | SO$_2$ | — | Me |
| 12-8 | 1-Me-c-Pr | CN | CO | SO$_2$ | — | H |

TABLE 13

(V = V1, Z = Z4):

| Ex. | R | R1 | v | U² | (R¹²)ᵣ | U¹ | (R¹⁶)ₙ |
|---|---|---|---|---|---|---|---|
| 13-1 | H | c-Pr | 1 | SO₂ | 2,5-DiMe | 3,4-diMe-pyrazol-1-yl (N-Me) | — |
| 13-2 | H | c-Pr | 1 | SO₂ | 2,5-DiMe | 3,4-diMe-pyrazol-1-yl (N-Et) | — |
| 13-3 | H | c-Pr | 2 | SO₂ | 2,5-DiMe | 3,4-diMe-pyrazol-1-yl (N-Me) | — |
| 13-4 | H | c-Pr | 2 | SO₂ | 2,5-DiMe | 3,4-diMe-pyrazol-1-yl (N-Et) | — |
| 13-5 | H | 1-Me-c-Pr | 1 | SO₂ | 2,5-DiMe | 3,4-diMe-pyrazol-1-yl (N-Me) | — |
| 13-6 | H | 1-Me-c-Pr | 1 | SO₂ | 2,5-DiMe | 3,4-diMe-pyrazol-1-yl (N-Et) | — |

TABLE 14

(V = V2, Z = Z4):

| Ex. | R2 | R3 | R4 | v | U² | (R¹²)ᵣ | U¹ | (R¹⁶)ₙ |
|---|---|---|---|---|---|---|---|---|
| 14-1 | H | H | Et | 1 | SO₂ | 2,5-DiMe | 3,4-diMe-pyrazol-1-yl (N-Me) | — |
| 14-2 | H | H | Et | 1 | SO₂ | 2,5-DiMe | 3,4-diMe-pyrazol-1-yl (N-Et) | — |

TABLE 14-continued
(V = V2, Z = Z4):
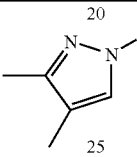
| Ex. | R2 | R3 | R4 | v | U² | (R¹²)ᵣ | U¹ | (R¹⁶)ₙ |
|---|---|---|---|---|---|---|---|---|
| 14-3 | H | SO₂-(4-Me)Ph | Et | 1 | SO₂ | 2,5-DiMe | 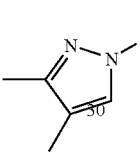 | — |
| 14-4 | H | SO₂Me | Et | 1 | SO₂ | 2,5-DiMe | 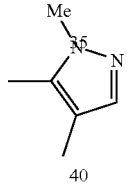 | — |
| 14-5 | H | H | Et | 1 | SO₂ | 2,5-DiMe | 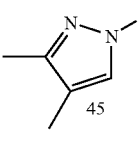 | — |
| 14-6 | H | H | Et | 2 | SO₂ | 2,5-DiMe | 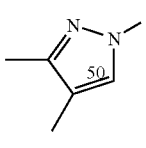 | — |
| 14-7 | H | H | Et | 2 | SO₂ | 2,5-DiMe | 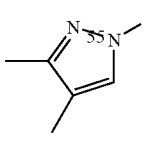 | — |
| 14-8 | H | H | Me | 1 | SO₂ | 2,5-DiMe | 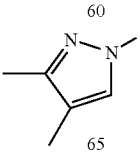 | — |
| 14-9 | H | H | Me | 1 | SO₂ | 2,5-DiMe |  | — |

TABLE 15

(V = V3, Z = Z4):

| Ex. | (R5)$_o$ | R6 | V | U$^2$ | (R$^{12}$)$_r$ | U$^1$ | (R$^{16}$)$_n$ |
|---|---|---|---|---|---|---|---|
| 15-1 | — | OH | 1 | SO$_2$ | 2,5-DiMe | 3,4-diMe-pyrazol-1-yl (N-Me) | — |
| 15-2 | — | OH | 1 | SO$_2$ | 2,5-DiMe | 3,4-diMe-pyrazol-1-yl (N-Et) | — |
| 15-3 | — | OH | 1 | SO$_2$ | 2,5-DiMe | 5-Cl-3,4-diMe-pyrazol-1-yl (N-Et) | — |
| 15-4 | 5-Me | OH | 1 | SO$_2$ | 2,5-DiMe | 3,4-diMe-pyrazol-1-yl (N-Me) | — |
| 15-5 | 5-Me | OH | 2 | SO$_2$ | 2,5-DiMe | 3,4-diMe-pyrazol-1-yl (N-Me) | — |
| 15-6 | — | OH | 1 | SO$_2$ | 2,5-DiMe | 1-Me-3,4-diMe-pyrazol-5-yl | — |
| 15-7 | — | OH | 2 | SO$_2$ | 2,5-DiMe | 3,4-diMe-pyrazol-1-yl (N-Et) | — |

TABLE 16

(V = V4, Z = Z4):

| Ex. | R7 | R8 | V | U$^2$ | (R$^{12}$)$_r$ | U$^1$ | (R$^{16}$)$_n$ |
|---|---|---|---|---|---|---|---|
| 16-1 | c-Pr | CN | 1 | SO2 | 2,5-DiMe | 3,4-diMe-pyrazol-1-yl (N-Me) | — |
| 16-2 | 1-Me-c-Pr | CN | 1 | SO2 | 2,5-DiMe | 3,4-diMe-pyrazol-1-yl (N-Me) | — |
| 16-3 | c-Pr | CN | 1 | SO2 | 2,5-DiMe | 3,4-diMe-pyrazol-1-yl (N-Et) | — |
| 16-4 | 1-Me-c-Pr | CN | 1 | SO2 | 2,5-DiMe | 3,4-diMe-pyrazol-1-yl (N-Et) | — |

The safeners (antidotes) of the formulae (II)–(VII) and the compounds of group (b), for example safeners of the abovementioned groups a) to h), reduce or prevent phytotoxic effects which may occur when using the herbicidal active substances of the formula (I) in crops of useful plants without substantially affecting the efficacy of these herbicidal active substances against harmful plants. This allows the field of application of conventional crop protection products to be widened quite considerably and to be extended to, for example, crops such as wheat, barley, maize and other crops in which use of the herbicides was hitherto impossible, or only limited, that is to say at low rates and with a restricted spectrum.

The herbicidal active substances and the mentioned safeners can be applied together (as a readymix or by the tank mix method) or in succession in any desired sequence. The weight ratio of safener:herbicidal active substance may vary within wide limits and is preferably in the range of from 1:100 to 100:1, in particular 1:10 to 10:1. The optimum amounts of herbicidal active substance and safener which are used in each case depend on the type of the herbicidal active substance used or on the safener used and on the species of the crop stand to be treated and can be determined in each individual case by simple routine preliminary experiments.

The main fields of application for the combinations according to the invention are, in particular, maize and cereal crops such as, for example, wheat, rye, barley, oats, rice, sorghum, but also cotton and soybeans, preferably cereals, rice and maize.

Depending on their properties, the safeners employed in accordance with the invention can be used for pretreating the seed of a crop plant (seed dressing), or be incorporated into the seed furrows prior to sowing or applied together with the herbicide before or after plant emergence. The pre-emergence treatment includes not only treatment of the area under cultivation prior to sowing and treatment of the areas under cultivation where the seeds have been planted but the plants have not yet emerged. The joint application together with the herbicide is preferred. To this end, tank mixes or readymixes may be employed.

The application rates of safener required may vary within wide limits depending on indication and herbicidal active substance used and are generally in the range of from 0.001 to 5 kg, preferably 0.005 to 0.5 kg, of active substance per hectare.

The present invention therefore also relates to a method of protecting crop plants from phytotoxic side effects of herbicides of the formula (I) which comprises applying an antidote-effective amount of a compound of the formula (II), (III), (IV), (V), (VI), (VII) and/or (selected from the group (b)) to the plants, plant seeds or the area under cultivation, either before, after or simultaneously with, the herbicidal active substance A of the formula (I).

The herbicide/safener combination according to the invention may also be employed for controlling harmful plants in crops of genetically engineered plants which are either known or still to be developed. As a rule, the transgenic plants are distinguished by particular, advantageous properties, for example by resistance to certain crop protection agents, resistance to plant diseases or pathogens causing plant diseases such as particular insects or microorganisms such as fungi, bacteria or viruses. Other particular properties relate, for example, to the harvested material in terms of quantity, quality, storing properties, composition and specific constituents. Thus, there are known transgenic plants with an increased starch content or with an altered starch quality, or those where the harvested material has a different fatty acid composition.

The use of the combinations according to the invention in economically important transgenic crops of useful plants and ornamentals, for example cereals such as wheat, barley, rye, oats, sorghum and millet, rice, cassava and maize, or else crops of sugar beet, cotton, soya, oilseed rape, potatoes, tomatoes, peas and other vegetables.

When the combinations according to the invention are applied in transgenic crops, effects on harmful plants to be observed in other crops are frequently accompanied by effects which are specific for application in the transgenic crop in question, for example an altered or specifically widened weed spectrum which can be controlled, altered application rates which may be used, preferably good compatibility with the herbicides to which the transgenic crop is resistant, and altered growth and yield of the transgenic crop plants.

The invention therefore also relates to the use of the combination according to the invention for controlling harmful plants in transgenic crop plants.

The safeners of the formulae (III)–(VII) and of group (b) and their combinations with one or more of the abovementioned herbicidal active substances of the formula (II) can be formulated in various ways, depending on the biological and/or chemico-physical parameters specified. Examples of possible formulations which are suitable are:

Wettable powders (WP), emulsifiable concentrates (EC), water-soluble powders (SP), water-soluble concentrates (SL), concentrated emulsions (BW) such as oil-in-water and water-in-oil emulsions, sprayable solutions or emulsions, capsule suspensions (CS), oil- or water-based dispersions (SC), suspoemulsions, suspension concentrates, dusts (DP), oil-miscible solutions (OL), seed-treatment products, granules (GR) in the form of microgranules, spray granules, coated granules and adsorption granules, granules for soil application or broadcasting, water-soluble granules (SG), water-dispersible granules (WG), ULV formulations, microcapsules and waxes.

These individual formulation types are known in principle and described, for example, in: Winnacker-Küchler, "Chemische Technologie" [Chemical Technology], Volume 7, C. Hauser Verlag Munich, $4^{th}$ Edition 1986; Wade van Valkenburg, "Pesticide Formulations", Marcel Dekker N.Y., 1973; K. Martens, "Spray Drying Handbook", 3rd Edition 1979, G. Goodwin Ltd. London.

The formulation auxiliaries which may be required, such as inert materials, surfactants, solvents and other additives are also known and described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-Active Ethylene Oxide Adducts], Wiss. Verlagsgesell., Stuttgart 1976; Winnacker-Küchler, "Chemische Technologie" [Chemical Technology], Volume 7, C. Hauser Verlag Munich, $4^{th}$ Edition 1986.

Based on these formulations, it is also possible to prepare combinations with other substances which act as crop protection agents, such as insecticides, acaricides, herbicides, fungicides, and also with safeners, fertilizers and/or growth regulators, for example in the form of a readymix or tank mix.

Wettable powders are preparations which are uniformly dispersible in water and which, besides the active substance, also comprise ionic and/or nonionic surfactants (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate, or else sodium oleoylmethyltaurinate, in addition to a diluent or inert substance. To prepare the wettable powders, the herbicidally active substances are ground finely, for example in customary apparatus such as hammer mills, blower mills and air-jet mills, and simultaneously or subsequently mixed with the formulation auxiliaries.

Emulsifiable concentrates are prepared, for example, by dissolving the active substance in an organic solvent, such as butanol, cyclohexanone, dimethylformamide, or else higher-boiling hydrocarbons such as saturated or unsaturated aliphatic hydrocarbons or alicyclic hydrocarbons, aromatics or mixtures of the organic solvents with the addition of one or more ionic and/or nonionic surfactants (emulsifiers). Examples of substances which can be used as emulsifiers are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters, for example sorbitan fatty acid esters or polyoxyethylene sorbitan esters, for example polyoxyethylene sorbitan fatty acid esters.

Dusts are generally obtained by grinding the active substance with finely distributed solid substances, for example talc, natural clays such as kaolin, bentonite and pyrophyllite, or diatomaceous earth.

Suspension concentrates can be water- or oil-based. They can be prepared, for example, by wet grinding using commercially available bead mills with or without an addition of surfactants, for example those which have already been mentioned above in the case of the other formulation types.

Emulsions, for example oil-in-water emulsions (EW), can be prepared, for example, by means of stirrers, colloid mills and/or static mixers using aqueous organic solvents in the presence or absence of surfactants which have already been mentioned above, for example, in the case of the other formulation types.

Granules can be prepared either by spraying the active substance onto adsorptive, granulated inert material or by applying active substance concentrates to the surface of carriers such as sand, kaolinites or granulated inert material with the aid of binders, for example polyvinyl alcohol, sodium polyacrylate or else mineral oils. Suitable active substances can also be granulated in the manner which is conventional for the preparation of fertilizer granules, if desired as a mixture with fertilizers. As a rule, water-dispersible granules are prepared by the customary processes such as spray drying, fluidized bed granulation, disk granulation, mixing with high-speed mixers, and extrusion without solid inert material.

For the preparation of disk, fluidized-bed, extruder and spray granules see, for example, processes in "Spray-Drying Handbook" $3^{rd}$ Ed. 1979, G. Goodwin Ltd., London; J. E. Browning, "Agglomeration", Chemical and Engineering 1967, pages 147 et seq.; "Perry's Chemical Engineer's Handbook", b $5^{th}$ Ed., McGraw-Hill, New York 1973, p. 8–57.

For further details on the formulation of crop protection products see, for example, G. C. Klingman, "Weed Control as a Science", John Wiley and Sons, Inc., New York, 1961, pages 81–96 and J. D. Freyer, S. A. Evans, "Weed Control Handbook", $5^{th}$ Ed., Blackwell Scientific Publications, Oxford, 1968, pages 101–103.

As a rule, the agrochemical preparations comprise 0.1 to 99% by weight, in particular 0.1 to 95% by weight, of active substances of the formula (II)–(VII) and/or (b) or of the herbicide/antidote mixture of active substances (I) and (II) –(VII) and/or (b) and 1 to 99.9% by weight, in particular 5 to 99.8% by weight of a solid or liquid additive and 0 to 25% by weight, in particular 0.1 to 25% by weight of a surfactant.

In wettable powders, the active substance concentration is, for example, approximately 10 to 90% by weight, the remainder to 100% by weight being composed of customary formulation components. In the case of emulsifiable concentrates, the concentration of active substance is approximately 1 to 80% by weight. Formulations in the form of dusts comprise 1 to 20% by weight of active substance, sprayable solutions comprise approximately 0.2 to 20% by weight of active substance. In the case of granules, such as water-dispersible granules, the active substance content depends partly on whether the active compound is in liquid or solid form. The active substance content of the water-dispersible granules is, for example, between 10 and 90% by weight.

Besides this the abovementioned formulations of active substances may comprise, if appropriate, the adhesives, wetting agents, dispersants, emulsifiers, penetrants, preservatives, antifreeze agents, solvents, fillers, carriers, colorants, antifoams, evaporation inhibitors and pH and viscosity regulators which are customary in each case.

Components which can be used in combination with the herbicide/safener mixtures according to the invention in mixed formulations or in tank mixes are, for example, known active substances as they are described, for example, in Weed Research 26, 441–445 (1986), or "The Pesticide Manual", $10^{th}$ edition, The British Crop Protection Council, 1994, and the literature cited therein. Examples of active substances which may be mentioned as herbicides which are known from the literature and which can be combined with the mixtures according to the invention are the following (note: either the common names in accordance with the International Organization for Standardization (ISO) or the chemical names, if appropriate together with a customary code number, of the compounds are given): acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azafenidine (DPX-R6447), azimsulfuron (DPX-A8947); aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofluor; benzoylprop-ethyl; benzthiazuron; bialaphos; bifenox; bispyribac-sodium (KIH-2023), bromacil; bromobutide; bromofenoxim; bromoxynil; bromuron; buminafos; busoxinone; butachlor; butamifos; butenachlor; buthidazole; butralin; butroxydim (ICI-0500), butylate; cafenstrole (CH-900); carbetamide; cafentrazone; CDAA, i.e. 2-chloro-N,N-di-2-propenylacetamide; CDEC, i.e. 2-chloroallyl diethyldithiocarbamate; chlomethoxyfen; chloramben; chloransulam-methyl (XDE-565), chlorazifop-butyl, chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthaldimethyl; chlorthiamid; cinidonethyl, cinmethylin; cinosulfuron; clefoxydim, clethodim; clodinafop and its ester derivatives (e.g. clodinafop-propargyl); clomazone; clomeprop; cloproxydim; clopyralid; cumyluron (JC 940); cyanazine; cycloate; cyclosulfamuron (AC 014); cycloxydim; cycluron; cyhalofop and its ester derivatives (e.g. butyl ester, DEH-112); cyperquat; cyprazine; cyprazole; 2,4-DB; dalapon; desmedipham; desmetryn; diallate; dicamba; dichlobenil; dichlorprop; diclofop and its esters such as diclofop-methyl; diclosulam (XDE-564), diethatyl; difenoxuron; difenzoquat; diflufenican; diflufenzopyr-sodium (SAN-835H), dimefuron; dimethachlor; dimethametryn; dimethenamid (SAN-582H); dimethazone, 5-(4,6-dimethylpyrimidin-2-yl-carbamoylsulfamoyl)-1-(2-pyridyl)-pyrazole-4-carboxylate (NC-330); clomazon; dimethipin; dimetrasulfuron, dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-1H-pyrazole-4-carboxamide; endothal; epoprodan (MK-243), EPTC; esprocarb; ethalfluralin; ethametsulfuron-methyl; ethidimuron; ethiozin; ethofumesate; F5231, i.e. N-[2-chloro-4-fluoro-5-[4-(3-fluorpropyl)-4,5-dihydro-5-oxo-1H-tetrazol-1-yl]phenyl]ethanesulfonamide; ethoxyfen and its esters (e.g. ethyl ester, HN-252); ethoxysulfuron (disclosed in EP 342569) etobenzanid (HW 52); 3-(4-ethoxy-6-ethyl-1,3,5-triazin-2-yl)-1-(2,3-dihydro-1,1-di-oxo-2-methylbenzo[b]thiophene-7-sulfonyl)urea (EP-A 079 683); 3-(4-ethyl-6-methoxy-1,3,5-triazin-2-yl)-1-(2,3-dihydro-1,1-dioxo-2-methylbenzo[b]thiophene-7-sulfonyl)urea (EP-A 079 683); fenoprop; fenoxan, fenoxaprop and fenoxaprop-P and their esters, e.g. fenoxaprop-P-ethyl and fenoxaprop-ethyl; fenoxydim; fentrazamide (NBA-061); fenuron; flamprop-methyl; flazasulfuron; flufenacet (BAY-FOE-5043), fluazifop and fluazifop-P, florasulam (DE-570) and their esters, e.g. fluazifop-butyl and fluazifop-P-butyl; fluazolate (Mon-48500), fluchloralin; flucarbazone-sodium; flumetsulam; flumeturon; flumiclorac and their esters (e.g. pentyl ester, S-23031); flumioxazin (S-482); flumipropyn; flupoxam (KNW-739); fluorodifen; fluoroglycofen-ethyl; flupropacil (UBIC-4243); flupyrsulfuron-methyl sodium (DPX-KE459), fluridone; flurochloridone; fluroxypyr; flurtamone; fluthiacet-methyl (KIH-9201), fomesafen; fosamine; furyloxyfen; glufosinate; glyphosate; halosafen; halosulfuron and its esters (e.g. methyl ester, NC-319); haloxyfop and its esters; haloxyfop-P (=R-haloxyfop) and its esters; hexazinone; imazamethabenz-methyl; imazamox (AC-299263), imazapyr; imazaquin and salts such as the ammonium salt; imazethamethapyr; imazethapyr; imazosulfuron; iodosulfuron (methyl-4-iodo-2-[3-(4-methoxy-6-methyl-1,3,5-triazin-2-yl)ureidosulfonyl]-benzoate, sodium salt, WO 92/13845); ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metobenzuron, methyl-2-[3-(4,6-dimethoxypyrimidin-2-yl)ureidosulfonyl]-4-methanesulfonamidomethylbenzoate (WO 95/10507); methobenzuron; metobromuron; metolachlor; S-metolachlor, metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; N,N-dimethyl-2-[3-(4,6-dimethoxypyrimidin-2-yl)ureidosulfonyl]-4-formylaminobenzamide (WO 95/01344); naproanilide; napropamide; naptalam; NC 310, i.e. 4-(2,4-dichlorobenzoyl)-1-methyl-5-benzyloxypyrazole; neburon; nicosulfuron; nipyraclofen; nitralin; nitrofen; nitrofluorfen; norflurazon; orbencarb; oryzalin; oxadiargyl (RP-020630); oxadiazon; oxaziclomefone (MY-100), oxyfluorfen; oxasulfuron (CGA-277476), paraquat; pebulate; pendimethalin; pentoxazone (KPP-314), perfluidone; phenisopham; phenmedipham; picloram; piperophos; piributicarb; pirifenopbutyl; pretilachlor; primisulfuron-methyl; pracarbazone-sodium; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyraflufen-ethyl (ET-751), pyrazon; pyrazosulfuron-ethyl; pyrazoxyfen; pyribenzoxim, pyridafol; pyridate; pyriminobac-methyl (KIH6127), pyrithiobac (KIH-2031); pyroxofop and its esters (e.g. propargyl ester); quinclorac; quinmerac; quinofop and its ester derivatives, quizalofop and quizalofop-P and their ester derivatives e.g. quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]-propanoic acid and its methyl ester; sulfentrazon (FMC-97285, F-6285); sulfazuron; sulfometuron-methyl; sulfosate (ICI-A0224); sulfosulfuron (MON-37500), TCA; tebutam (GCP-5544); tebuthiuron; tepraloxydim (BAS-620H), terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-124085); thifensulfuron-methyl; thiobencarb; thiocarbazil; tralkoxydim; tri-allate; triasulfuron, triaziflam (DH-1105); triazofenamide; tribenuron-methyl; triclopyr; tridiphane; trietazine; trifluralin; triflusulfuron and esters (e.g. methyl ester, DPX-66037); trimeturon; tsitodef; vernolate; WL 110547, i.e. 5-phenoxy-1-[3-(trifluoromethyl)phenyl]-1H-tetrazole; UBH-509; D489; LS 82–556; KPP-300; KPP-421, MT-146, NC-324; KH-218; DPX-N8189; DOWCO-535; DK-8910; V-53482; PP-600; MBH-001.

For use, the formulations which are in commercially available form are, if desired, diluted in the customary manner, for example using water in the case of wettable powders, emulsifiable concentrates, dispersions and water-dispersible granules. Preparations in the form of dusts, soil granules, granules for broadcasting and sprayable solutions are usually not diluted any further with other inert substances prior to use.

The necessary application rate of the herbicides of the formula (I) varies with the external conditions such as, inter alia, temperature, humidity and the nature of the herbicide used. It may be varied within wide limits, for example between 0.001 and 10.0 kg/ha or more of active ingredient, but it is preferably between 0.005 and 5 kg/ha.

The examples which follow are intended to illustrate the invention:

A. FORMULATION EXAMPLES a) A dust is obtained by mixing 10 parts by weight of a compound of the formula (II)–(VII) and/or (from amongst group (b)) or of an active substance mixture of a herbicidal active substance of the formula (I) and a safener of the formula (II)–(VII) and/or from amongst group (b) and 90 parts by weight of talc as inert substance and comminuting the mixture in a hammer mill.

b) A wettable powder which is readily dispersible in water is obtained by mixing 25 parts by weight of a compound of the formula (II), (III), (IV) and/or (B(b)) or of an active substance mixture of a herbicidal active substance of the formula (I) and a safener of the formula (II), (III), (IV) and/or from amongst group B(b), 64 parts by weight of kaolin-containing quartz as inert material, 10 parts by weight of potassium lignosulfonate and 1 part by weight of sodium oleoylmethyltaurinate as wetter and dispersant and grinding the mixture in a pinned-disk mill.

c) A dispersion concentrate which is readily dispersible in water is obtained by mixing 20 parts by weight of a compound of the formula (II)–(VII) and/or from amongst group (b) or of an active substance mixture of a herbicidal active substance of the formula (I) and a safener of the formula (II)–(VII) and/or from amongst group (b), 6 parts by weight of alkylphenol polyglycol ether (®Triton X 207), 3 parts by weight of isotridecanol polyglycol ether (8 EO) and 71 parts by weight of paraffinic mineral oil (boiling range, for example, approx. 255 to above 277° C.) and grinding the mixture in a ball mil to a fineness of below 5 microns.

d) An emulsifiable concentrate is obtained from 15 parts by weight of a compound of the formula (II)–(VII) and/or from amongst group (b) or of an active substance mixture of a herbicidal active substance of the formula (I) and a safener of the formula (II)–(VII) and/or from amongst group (b), 75 parts by weight of cyclohexanone as solvent and 10 parts by weight of ethoxylated nonylphenol as emulsifier.

e) Water-dispersible granules are obtained by mixing
   75 parts by weight of a compound of the formula (II)–(VII) and/or from amongst the group (b) or of an active substance mixture of a herbicidal active substance of the formula (I) and a safener of the formula (II)–(VII) and/or from amongst group b,
   10" of calcium lignosulfonate
   5" of sodium lauryl sulfate,
   3" of polyvinyl alcohol and
   7" of kaolin, grinding the mixture on a pinned-disk mill and granulating the powder in a fluidized bed by spraying on water as the granulation liquid.

f) Water-dispersible granules are also obtained by homogenizing and precomminuting, on a colloid mill,
   25 part(s) by weight of a compound of the formula (II)–(VII) and/or from amongst group (b) or of an active substance mixture of a herbicidal active substance of the formula (I) and a safener of the formula (II)–(VII) and/or from amongst group (b)
   5" of sodium 2,2'-dinaphthylmethane-6,6'-disulfonate
   2" of sodium oleoylmethyltaurinate,
   1" of polyvinyl alcohol,
   17" of calcium carbonate and
   50" of water,
   subsequently grinding the mixture on a bead mill and atomizing and drying the resulting suspension in a spray tower by means of a single-substance nozzle.

BIOLOGICAL EXAMPLES

1. Scoring the Damage

The damage to the plants is assessed visually in comparison with control plants using a scale of 0–100%:
0%=no noticeable effect in comparison with the untreated plant,
100%=treated plant dies.

2. Pre-emergence Herbicide Action and Safener Action

Seeds of monocotyledonous and dicotyledonous weed plants of crop plants are placed in sandy loam soil in plastic pots of 9 cm diameter and covered with soil. Alternatively, weeds found in rice cultivation under paddy rice conditions are, for the test, cultivated in waterlogged soil, the pots being filled with such an amount of water that the water reaches the soil surface or floods it by a few millimeters. The active substance combinations according to the invention, of herbicide and safener, which are formulated as emulsion concentrates and, in parallel experiments, the individual active substances formulated analogously are then applied to the surface of the soil cover in the form of emulsions at a water application rate of 300 l/ha (converted) or, in the case of rice, poured into the irrigation water, in each case in various dosages.

After the treatment, the pots are placed in the greenhouse and kept under good growth conditions. After the test plants have emerged after a test period of 3–4 weeks, the damage to the plants, or emergence damage, is scored visually by comparison with untreated controls. As illustrated by the test results, the herbicidal compositions according to the invention have a good herbicidal pre-emergence action against a broad spectrum of grass weeds and dicotyledonous weeds, while damage to crop plants such as maize, rice, wheat or barley or other cereals is markedly reduced by comparison with the use of the individual herbicides without safener, i.e. the herbicide damage is reduced by 30% up to 100%.

3. Post-emergence Herbicide Action and Safener Action

Seeds of monocotyledonous and dicotyledonous weed plants and of crop plants are placed in sandy loam soil in plastic pots, covered with soil and grown in the greenhouse under good growth conditions. Alternatively, weeds found in rice cultivation and rice are grown, for the test under paddy rice conditions, in pots in which water floods the soil surface by up to 2 cm, and cultivated during the growth phase. Approx. three weeks after sowing, the test plants are treated in the three-leaf stage. The active substance combinations according to the invention of herbicide and safener which are formulated as emulsion concentrates and, in parallel experiments, the individual active substances which are formed analogously are sprayed onto the green parts of the plants in various dosages at a water application rate of 300 l/ha (converted) and, after the test plants have been left in the greenhouse for three weeks under ideal growth conditions, the effect of the products was scored visually by comparison with untreated controls. In the case of rice or weeds found in rice cultivation, the active substances are also added direct to the irrigation water (application analogously to the so-called granule application) or sprayed onto plants and into the irrigation water. As the results, in particular those shown in Tables 17 and 18, demonstrate, the herbicidal compositions according to the invention have a goods herbicidal post-emergence activity against a broad spectrum of grass weeds and dicotyledonous weeds, while damage to crop plants such as maize, rice, wheat or barley or other cereals is markedly reduced by comparison with the use of the individual herbicides without safener, i.e. the herbicide damage is reduced by 30% up to 100%..

TABLE 17

| Compound No. Herbicide/Safener | Dosage [g/ha] Herbicide Safener | Damage [%] in wheat Variety "RALLE" |
|---|---|---|
| 7-14 | 50 | 30 |
|  | 25 | 25 |
| 7-14 / Ph₂C(O-N=)CH=C-CO₂Et | 50 + 50 | 5 |
|  | 25 + 25 | 0 |

TABLE 18

| Compound No. Herbicide/Safener | Dosage [g/ha] Herbicide Safener | Damage [%] in maize Variety "FELIX" | Variety "DEA" |
|---|---|---|---|
| 5-10 | 200 | 88 | 25 |
|  | 100 | 65 | 10 |
|  | 50 | 30 | 0 |
| 5-10 /  | 200 + 100 | 40 | 0 |
|  | 50 + 25 | 0 | 0 |
| 5-10 / 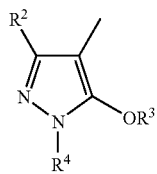 | 200 + 100 | 20 | 0 |
|  | 100 + 50 | 0 | 0 |
| 5-10 / 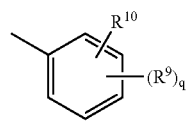 | 200 + 100 | 30 | 0 |
|  | 50 + 25 | 0 | 0 |
| 5-10 / (structure) | 200 + 100 | 5 | 0 |
|  | 50 + 25 | 0 | 0 |

What is claimed is:

1. A herbicidally active composition comprising a mixture of:

A. a herbicidally active amount of one or more compounds of the formula (I)

$$V \overset{O}{\underset{}{\text{—}}} Z \quad (I)$$

in which

V is a radical of the formula, (V2)

(pyrazole structure with $R^2$, methyl, $OR^3$, $R^4$ substituents)

where the symbols and indices have the following meanings:

$R^2$ is hydrogen, $(C_1-C_4)$alkyl, $(C_1-C_4)$alkoxy, $(C_1-C_4)$haloalkyl, halogen, $(C_1-C_4)$haloalkoxy, cyano, nitro;

$R^3$ is hydrogen or an optionally substituted $(C_1-C_4)$alkyl, $(C_2-C_4)$alkenyl, $(C_2-C_4)$alkynyl, $(C_1-C_4)$alkoxy-$(C_1-C_4)$alkyl, $(C_1-C_4)$alkylcarbonyl, $(C_1-C_4)$alkylsulfonyl, $(C_1-C_4)$haloalkylsulfonyl, arylsulfonyl, arylcarbonyl-$(C_1-C_4)$alkyl radical, or an aryl$(C_1-C_4)$alkyl radical;

$R^4$ is hydrogen or an optionally substituted $(C_1-C_7)$alkyl, $(C_2-C_7)$alkenyl, $(C_2-C_7)$alkynyl radical or aryl radical; and Z is a radical (Z1)

(Z1)

(phenyl structure with methyl, $R^{10}$, $(R^9)_q$ substituents)

where the symbols and indices have the following meanings:

$R^9$ is nitro, amino, cyano, halogen or an optionally substituted $(C_1-C_8)$alkyl, $(C_2-C_8)$alkenyl, $(C_2-C_8)$alkynyl, $(C_1-C_8)$alkoxycarbonyl, $(C_1-C_8)$alkylsulfonyl, $(C_1-C_8)$alkylsulfinyl, $(C_1-C_8)$alkylthio, aryl, arylsulfonyl, arylsulfinyl, arylthio, aryloxy, $(C_1-C_8)$alkoxy, $(C_1-C_8)$alkoxy-$(C_1-C_8)$alkoxy, $(C_1-C_8)$alkylcarbonyl, $(C_1-C_8)$alkylaminosulfonyl, $(C_1-C_8)$dialkylaminosulfonyl, $(C_1-C_8)$alkylcarbamoyl, $(C_1-C_8)$dialkylcarbamoyl, $(C_1-C_8)$alkoxy-$(C_1-C_8)$alkyl, $(C_1-C_8)$alkylamino, or $(C_1-C_8)$dialkylamino radical;

$R^{10}$ is a radical of formula

q is 0, 1, 2, 3, or 4; and

B. an antidote-effective amount of one or more compounds selected from the groups consisting of a):

a) compounds of the formulae (II) and (III)

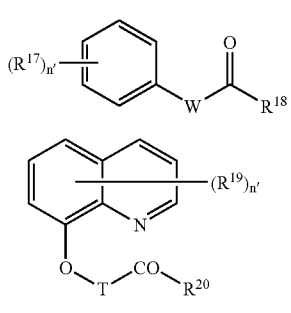

where the symbols and indices have the following meanings:

n' is a natural number from 1 to 5,

T is a ($C_1$ or $C_2$)-alkanediyl chain which is unsubstituted or substituted by one or two $(C_1-C_4)$alkyl radicals or by $[(C_1-C_3)$-alkoxy]carbonyl, W is a radical of the formula

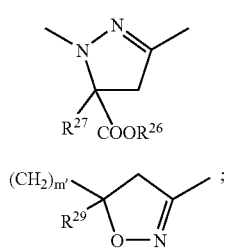

$R^{17}$, $R^{19}$ are identical or different hydrogen, halogen, $(C_1-C_4)$alkyl, $(C_1-C_4)$alkoxy, nitro or $(C_1-C_4)$haloalkyl;

$R^{18}$, $R^{20}$ are identical or different $OR^{24}$, $SR^{24}$ or $NR^{24}R^{25}$ or a saturated or unsaturated 3- to 7-membered heterocycle having at least one nitrogen atom and up to 3 hetero atoms which is linked to the carbonyl group in (II) or (III) via the nitrogen atom and which is unsubstituted or substituted by radicals from the group consisting of $(C_1-C_4)$alkyl, $(C_1-C_4)$alkoxy or optionally substituted phenyl;

$R^{24}$ is hydrogen or an unsubstituted or substituted aliphatic hydrocarbon radical;

$R^{25}$ is hydrogen, $(C_1-C_6)$alkyl, $(C_1-C_6)$alkoxy or substituted or unsubstituted phenyl;

$R^{26}$ is hydrogen, $(C_1-C_8)$alkyl, $(C_1-C_8)$haloalkyl, $(C_1-C_4)$alkoxy-$(C_1-C_4)$alkyl, $(C_1-C_6)$hydroxyalkyl, $(C_3-C_{12})$cycloalkyl or tri-$(C_1-C_4)$-alkylsilyl;

$R^{27}$, $R^{29}$ are identical or different hydrogen, $(C_1-C_8)$alkyl, $(C_1-C_6)$haloalkyl, $(C_3-C_7)$cycloalkyl or phenyl which is unsubstituted or substituted by one or more radicals selected from the group consisting of halogen, $(C_1-C_4)$alkyl, $(C_1-C_4)$alkoxy, nitro, $(C_1-C_4)$haloalkyl and $(C_1-C_4)$haloalkoxy; and m' is 0 or 1;

inclusive of the stereoisomers and of the salts conventionally used in agriculture.

2. The herbicidally active composition according to claim 1 wherein the compound of formula I is

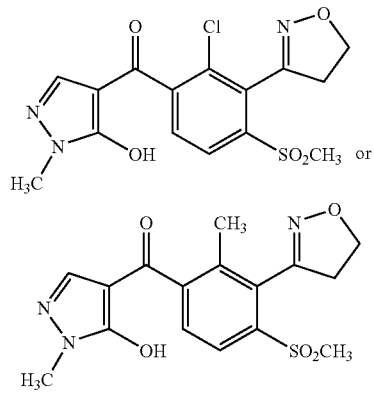

and the antidote is

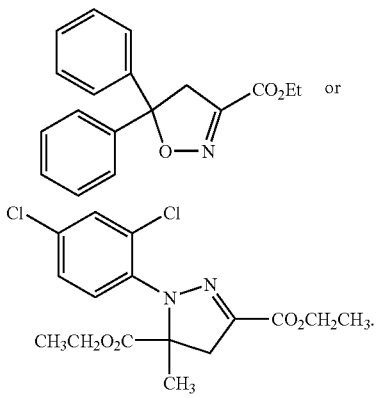

3. The herbicidally active compound according to claim 1 wherein the compound of formula I is

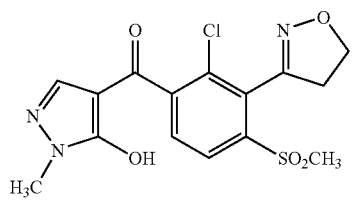

and the antidote is
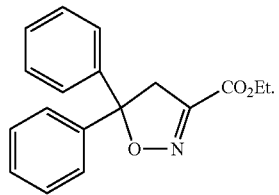
4. The herbicidally active compound according to claim 1 wherein the compound of formula I is
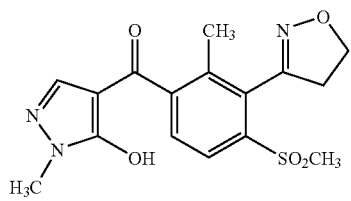
and the antidote is
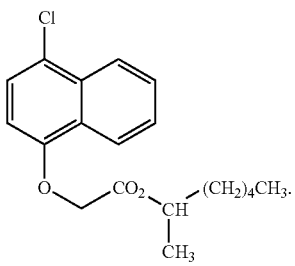
* * * * *